(12) United States Patent
Palacios et al.

(10) Patent No.: US 12,215,376 B2
(45) Date of Patent: Feb. 4, 2025

(54) MITOCHONDRIAL NUCLEIC ACID DEPLETION AND DETECTION

(71) Applicants: PROGENIKA BIOPHARMA, S.A., Derio (ES); UEA ENTERPRISES LIMITED, Norwich (GB)

(72) Inventors: Lourdes Palacios, Derio (ES); Nerea Bartolome, Derio (ES); Antonio Martinez, Derio (ES); Justin Joseph O'Grady, Norwich (GB); Gemma Louise Kay, Norwich (GB)

(73) Assignees: Progenika Biopharma, S.A., Derio (ES); UEA Enterprises Limited, Norwich (GB)

( * ) Notice: Subject to any disclaimer, the term of this patent is extended or adjusted under 35 U.S.C. 154(b) by 1002 days.

(21) Appl. No.: 17/253,448

(22) PCT Filed: Jun. 20, 2019

(86) PCT No.: PCT/EP2019/066397
§ 371 (c)(1),
(2) Date: Dec. 17, 2020

(87) PCT Pub. No.: WO2019/243536
PCT Pub. Date: Dec. 26, 2019

(65) Prior Publication Data
US 2021/0254135 A1 Aug. 19, 2021

(30) Foreign Application Priority Data
Jun. 21, 2018 (EP) ..................................... 18382457

(51) Int. Cl.
| | | |
|---|---|---|
| *C12Q 1/6806* | (2018.01) | |
| *G01N 1/40* | (2006.01) | |
| *C12N 15/10* | (2006.01) | |
| *C12Q 1/70* | (2006.01) | |

(52) U.S. Cl.
CPC ......... *C12Q 1/6806* (2013.01); *G01N 1/4044* (2013.01); *G01N 1/405* (2013.01); *C12N 15/1003* (2013.01); *C12Q 1/70* (2013.01)

(58) Field of Classification Search
None
See application file for complete search history.

(56) References Cited

U.S. PATENT DOCUMENTS

| 2005/0014128 A1 | 1/2005 | Ewert et al. |
| 2013/0189674 A1 | 7/2013 | Feehery et al. |
| 2014/0295418 A1 | 10/2014 | Goldrick et al. |

FOREIGN PATENT DOCUMENTS

| EP | 2 889 380 | * | 1/2015 |
| EP | 2889380 A1 | | 7/2015 |
| WO | WO 2016/100955 A2 | | 6/2016 |
| WO | WO 2016/169579 A1 | | 10/2016 |
| WO | WO 2018/109454 A1 | | 6/2018 |
| WO | WO 2019/079656 A1 | | 4/2019 |

OTHER PUBLICATIONS

Little, Clive, and Martin G. Rumsby. "Lysis of erythrocytes from stored human blood by phospholipase C (Bacillus cereus)." Biochemical Journal 188.1 (1980): 39-46.*
Parker, Jayme, and Jack Chen. "Application of next generation sequencing for the detection of human viral pathogens in clinical specimens." Journal of Clinical Virology 86 (2017): 20-26.*
Anonymous: "Selective Enrichment of Bacterial and Fungal DNA: Small, medium and large volumes: Removal of human DNA," Molzym, Sep. 26, 2014, Retrieved from the Internet on Jan. 24, 2018: URL:http://www.molzym.com/images/stories/pdf/2014 MolYsis web.pdf.
Feehery et al.: "A Method for Selectively Enriching Microbial DNA from Contaminating Vertebrate Host DNA," *Plos One*, 8(10): e76096, 2013, 13 pages.
Gu et al.: "Depletion of Abundant Sequences by Hybridization (DASH): using Cas9 to remove unwanted high-abundance species in sequencing libraries and molecular counting applications," *Genome Biol.*, 17: 41, 2016, 13 pages.
Hasan et al.: "Depletion of Human DNA in Spiked Clinical Specimens for Improvement of Sensitivity of Pathogen Detection by Next-Generation Sequencing," *J Clin Microbiol.*, 54 (4): 919-927, 2016.
Marotz et al.: "Improving saliva shotgun metagenomics by chemical host DNA Depletion," *Microbiome*, 6: 42, 2018, 9 pages.
Wilson et al.: "Actionable Diagnosis of Neuroleptospirosis by Next-Generation Sequencing," *N Engl J Med.*, 370:2408-2417, 2014.

* cited by examiner

*Primary Examiner* — Patrick T Lewis
(74) *Attorney, Agent, or Firm* — Klarquist Sparkman, LLP

(57) ABSTRACT

The present invention provides a method for depleting host nucleic acid in a biological sample, said sample having been previously obtained from an animal host and having been subjected to treatment to lyse host cells present in the sample, and having been subjected to a treatment to deplete nucleic acid released from host cells within said sample or otherwise to render such nucleic acid unidentifiable, the method comprising: (a) depleting host mitochondria or host mitochondrial DNA (mtDNA) present in the treated sample; and (b) extracting and/or analysing remaining nucleic acid from the treated sample. Also provided is a related kit comprising reagents for performing the method. Further claimed is a method for isolating mitochondrial DNA after host cells have been lysed and host cell nucleic acids have been removed from the sample.

19 Claims, 7 Drawing Sheets
Specification includes a Sequence Listing.

MITOCHONDRIAL NUCLEIC ACID DEPLETION AND DETECTION

CROSS REFERENCE TO RELATED APPLICATIONS

This application is the § 371 U.S. National Stage of International Application No. PCT/EP2019/066397, filed Jun. 20, 2019, which was published in English under PCT Article 21(2), which in turn claims priority from EP18382457.2, filed 21 Jun. 2018, the contents and elements of which are herein incorporated by reference for all purposes.

FIELD OF THE INVENTION

The present invention relates, in part, to methods for depleting host nucleic acid from a biological sample, in particular, to provide relative enrichment of non-host nucleic acid, such as pathogen DNA and/or RNA.

BACKGROUND TO THE INVENTION

Rapid and comprehensive infectious disease diagnostics are crucial for improved patient management and in the fight against antimicrobial resistance. Rapid diagnosis of life-threatening infectious diseases such as sepsis and pneumonia is paramount. These clinical syndromes have complex aetiologies and require pathogen recognition in challenging sample matrixes e.g. blood, sputum etc. Currently, the "gold standard" method for clinical diagnostics is microbial culture, which is labour intensive, has long turnaround times and poor clinical sensitivity. Currently available rapid molecular methods (e.g. PCR) improve turnaround time to result and sensitivity, but are limited by range and therefore rare pathogens and resistance markers can be problematic. In addition, currently available methods are designed to detect predefined pathogens and therefore many samples, e.g. having unknown or unexpected pathogens present, may not be correctly determined.

Shotgun metagenomic sequencing can detect and provide relative proportions of viruses, bacteria and fungi in a sample without any prior knowledge of the microbial community present, and is increasingly being used to investigate complex metagenomes in clinical samples.

A major barrier to the application of shotgun metagenomic sequencing to infection diagnosis is the large amount of human DNA present in clinical samples, which is often several orders of magnitude greater than the pathogen DNA present. Blood is a particularly challenging matrix for next generation sequencing (NGS)-based pathogen characterization due to the vast amount of human vs. pathogen nucleic acid (particularly DNA) present (ratio is typically $10^8:1$ to $10^9:1$, based upon $10^6$ leukocytes/ml [with ~6.6 pg DNA/cell] but as few as 1-10 colony forming units [CFU] of pathogen/ml [with ~10 fg DNA/cell]). A host DNA depletion of at least about $10^5$, potentially resulting in a human: pathogen DNA ratio of $10^3:1$, is required to facilitate NGS-based pathogen characterization, a level of depletion (giving rise to relative pathogen nucleic acid enrichment) not achieved by methods disclosed in the art, such as commercially available pathogen DNA enrichment methods (Looxster® Enrichment kit (Analytic Jena); NEBNext® Microbiome DNA Enrichment kit (NEB); MolYsis® Basic 5 kit (Molzym)).

Feehery et al., *PLOS ONE*, 2013, Vol. 8, No. 10, p.e76096, describes a method for selectively enriching microbial DNA from contaminating vertebrate host DNA. The method described exploits the differential CpG methylation density of host DNA vs. microbial DNA. A methyl-CpG binding domain (MBD) fused to the Fc region of a human antibody was used to remove human or fish host DNA from bacterial and prostatin DNA for subsequent sequencing and analysis. Sequence reads aligning to host genomes were found to have been decreased 50-fold, while bacterial and *Plasmodium* DNA sequence reads increased 8-11.5-fold.

WO2016/169579 describes a method, lysis solution and kit for selectively depleting animal nucleic acids in a sample.

US2014/0295418 describes methods and compositions for improving removal of ribosomal RNA from biological samples.

Gu et al., *Genome Biology* (2016), Vol. 17:41, pp. 1-13 describes depletion of abundant sequences by hybridisation (DASH), in which Cas9 is used to remove unwanted high-abundance species in sequencing libraries and molecular counting applications.

Hasan et al., *J. Clin. Microbiol.* (2016), Vol. 54, No. 4, pp. 919-927, describes depletion of human DNA in spiked clinical specimens for improvement of sensitivity of pathogen detection by next-generation sequencing.

WO2018/109454 describes a method for depleting host nucleic acid in a biological sample, and is incorporated herein by reference in its entirety. The method employs a cytolysin, such as *Clostridium perfringens* phospholipase C (NCB' GenPept Accession No. EDT77687, version EDT77687.1, date: 10 Apr. 2008, the amino acid sequence of which is incorporated herein by reference), to lyse an animal, particularly mammalian host cell substantially without lysing microbial cells present in the sample. The host nucleic acid—(NA), particularly DNA and RNA, released by the cytolysin treatment is then partially or completely depleted, for example by action of nuclease. The intact microbial cells are then isolated by centrifugation and collection of the cell pellet, the microbial cells lysed with a bacterial lysis buffer and microbial DNA extracted for subsequent analysis, e.g., by NGS techniques.

Despite these advances in the enrichment of pathogen nucleic acid from host cell-containing samples, there remains a need for alternative methods for enrichment of non-host, e.g. pathogen, nucleic acid from host cell-containing samples, including for methods that provide even greater enrichment, for example to facilitate infection diagnosis where low limit of detection (LOD) is required (e.g. sepsis) and/or where almost the whole genome of the pathogen is required (e.g. for antibiotic resistance genes detection, or the even more challenging detection of resistance-conferring mutations). The present invention seeks to provide solutions to these needs and provides further related advantages.

BRIEF DESCRIPTION OF THE INVENTION

The present inventors found that despite the host nucleic acid depletion, and consequent enrichment of microbial nucleic acid, provided by the method of WO2018/109454, a significant level of host (e.g. human) DNA remains after cytolsin and nuclease treatment. The present inventors sought to characterise this residual host DNA and, as described in the Examples herein, it was found that this residual host DNA was in large part host mitochondrial DNA (mtDNA). The present invention provides for partial or complete depletion of mitochondria and/or mitochondrial nucleic acid (mtNA), including mtDNA and mtRNA from the sample and consequent enrichment of non-host, e.g.

pathogen, nucleic acid, such as microbial DNA or RNA, thereby further enriching the level of non-host nucleic acid to facilitate analysis, including NGS-based analysis.

Accordingly, in a first aspect the present invention provides a method for depleting host nucleic acid in a biological sample, said sample having been previously obtained from an animal host and having been subjected to treatment to lyse host cells, optionally using a cytolysin, or an active variant thereof, and optionally having been subjected to a treatment to deplete nucleic acid released from host cells within said sample or otherwise to render such nucleic acid unidentifiable, the method comprising:

(a) depleting host mitochondria or host mitochondrial nucleic acid (mtNA) present in the treated sample; and
(b) extracting and/or analysing (e.g. sequencing) remaining nucleic acid from the treated sample.

In some embodiments step (a) comprises depleting host mitochondrial ribonucleic acid (mtRNA) and/or mtDNA present in the treated sample.

In some embodiments, the sample not having been previously subjected to treatment to deplete nucleic acid released from host cells with the sample, the method comprises a step of depleting nucleic acid released from host cells within the sample. The step of depleting nucleic acid released from host cells within the sample may be performed prior to, concurrent with, or following, the step of depleting host mitochondria or host mitochondrial nucleic acid (mtNA) present in the sample.

In some embodiments step (a) comprises adding a detergent to said treated sample. The detergent may be a plasma membrane permeabilising detergent. In particular, the detergent may comprise saponin, digitonin, Triton X-100, Nonidet, NP-40, Tween-20 and/or filipin. Saponin has previously been described as a plasma membrane selective permeabilising detergent. For example, Kuznetsov et al., *Nature Protocols,* 2008, Vol. 3, No. 6, pp. 965-976, report that digitonin, saponin and filipin are cholesterol-complex-forming agents that induce a loss of membrane integrity of the plasma membrane (see FIG. 1 of Kuznetsov et al.). Indeed, Kuznetsov et al. report that digitonin, saponin and filipin may be used to permeabilise a cell in order to isolate functional mitochondria for study. It was therefore surprising that the addition of saponin to cytolysin-treated mammalian cells, as described in the Examples herein, was found to render mammalian mitochondria sufficiently permeable that subsequent nuclease treatment depleted the mammalian mitochondrial NA.

In some embodiments the saponin has a sapogenin content of at least 5%, 6%, 7%, 8%, 9% or at least 10%. Sapogenins are the aglycones, or non-saccharide, portions of the family of natural products known as saponins. Sapogenins contain steroid or other triterpene frameworks as their key organic feature. Sapogenin content may be evaluated by techniques known in the art, such as by high performance liquid chromatography (HPLC) and/or GC/MS GC/FID (see Carelli et al., *New Phytologist,* 2015, Vol. 206, pp. 303-314 and references cited therein).

In some embodiments the saponin is added to said treated sample at a concentration of 2.5%, 2.0%, 1.5%, 1% or 0.5% w/v or less.

In some embodiments the saponin may comprise the saponin having the CAS number 8047-15-2. For example, Saponin 50019 from Tokyo Chemical Industry.

In some embodiments step (a) further comprises adding a nuclease to said treated sample. In some embodiments the nuclease is a DNAse or an RNAse or both a DNAse and an RNAse. The nuclease may be an endonuclease or an exonuclease. Preferred nucleases include HL-SAN (heat labile salt activated nuclease). It is specifically contemplated herein that the sample may or may not have been treated with a nuclease prior to step (a). For example, the sample may have been previously treated to lyse the host cells (using a cytolysin, a detergent or otherwise), then treated with a nuclease to deplete, e.g., released nuclear DNA. In such cases, step (a) may comprise adding a detergent (as described above) to the previously-treated sample and (i) allowing the previously added nuclease to deplete mtNA, (ii) adding further nuclease of the same type as that previously added in order to deplete mtNA, or (iii) adding further nuclease of a different type from that previously added in order to deplete mtNA.

In some embodiments step (a) comprises at least partial removal of host mitochondria by contacting the treated sample with an immobilised binding agent that selectively binds mitochondria. In particular, the binding agent may comprise an antibody, or binding fragment thereof, that selectively binds a protein or other accessible epitope present on the surface of the mitochondria (e.g. an outer membrane protein). In some embodiments the binding agent (e.g. antibody) selectively binds Mitochondrial import receptor subunit TOM22 homolog (TOM22). TOM22 has the UniProt accession number Q9NS69 (UniProt sequence last modified: 23 Jan. 2007). In particular, the method may comprise use of a commercial mitochondrial isolation kit, such as the human mitochondria isolation kit (Cat. No. 130-094-532 by Miltenyi Biotec, Surrey, UK). After cell lysis, mitochondria are magnetically labeled with Anti-TOM22 MicroBeads, human, which bind to the translocase of the outer mitochondrial membrane 22 protein (TOM22). The sample is loaded onto an MS or LS Column placed in its corresponding MACS Separator. Only magnetically labeled mitochondria are retained on the column, the eluate is therefore depleted in mitochondria.

In some embodiments step (a) comprises extraction of whole nucleic acids and further capturing of mitochondrial DNA using a panel of DNA and/or RNA and/or peptide nucleic acid (PNA) baits that target the host mitochondrial genome. PNAs may display high affinity for their target nucleic acid sequence, such as higher affinity that the corresponding DNA or RNA sequence has (Pellestor et al., *Curr. Pharm. Des.,* 2008, Vol. 14, No. 24, pp. 2439-2444). Preferably the baits hybridise to regions of the host (e.g. human) mitochondrial genome sequence. In this way mtDNA is captured and removed from the sample providing for relative enrichment of pathogen or other microbial nucleic acid.

In some embodiments step (a) comprises extraction of whole nucleic acids and further RNA-guided DNA endonuclease enzyme-mediated binding of host mitochondrial DNA using a single guide RNA (sgRNA) that targets a host mitochondrial DNA target sequence. In particular embodiments, the RNA-guided DNA endonuclease enzyme may be a CRISPR associated protein 9 (Cas9) enzyme, such as Cas9 Nuclease, *S. pyogenes* (M0386) from New England Biolabs (NEB), or a Cpf1 enzyme as disclosed in Zetsche et al., *Cell,* 2015, Vol. 163(3), pp. 759-771 (incorporated herein by reference). In some embodiments the RNA-guided DNA endonuclease enzyme (e.g. Cas9) may be inactive (e.g. substantially lacking endonuclease activity). In these embodiments, the inactive Cas9 is targeted to the mtDNA via appropriate sgRNA and the Cas9-mtDNA complex is selectively removed (e.g. using a binding agent that selectively binds Cas9).

In some embodiments step (a) comprises extraction of whole nucleic acids and further RNA-guided DNA endonuclease enzyme (e.g. CRISPR associated protein 9 (Cas9), Cas12, Cas13 or Cpf1)-mediated cleavage of host mitochondrial DNA using a single guide RNA (sgRNA) that targets a host mitochondrial DNA target sequence. In particular embodiments, the extracted NA is fragmented and specific sequences (adaptors) are added to the 5' and/or 3' ends of fragmented Nucleic Acids (NAs) by ligation or using a transposase. In these embodiments, the RNA-guided DNA endonuclease enzyme is targeted to the mtDNA via appropriate sgRNA and the mtDNA is cleaved. The resulting NAs are amplified by, for example, PCR using primers hybridizing to the adaptor sequences. Only the NAs not targeted by Cas9 will have intact adaptors on both ends of the same molecule, and so only these non-targeted NAs will be amplified. The cleaved NAs will not be amplified and, therefore, the mtDNA proportion will be reduced. An example of this approach for depleting target sequences has been described by Gu et al., *Genome Biology* (2016) 17:41.

In some embodiments the sample has previously been treated with a detergent or a cytolysin so as to lyse the host cells and release host nucleic acids, e.g., host nuclear DNA.

In some embodiments the treatment to which the sample has been subjected to lyse host cells is a treatment that is effective to lyse at least 3%, 4%, 5%, 10%, 15%, 20%, 25%, 30%, 35%, 40%, 45%, 50%, 55%, 60%, 65%, 70%, 75%, 80%, 85%, 90% or at least 95% of the host cells in the sample. As shown in Example 8 herein, the level of spontaneous lysis during normal sample preparation and storage was found to be below this level. Specifically contemplated herein are active methods intended to cause lysis to the host cells. Such methods lyse at least 3% of the host cells in the sample.

In some embodiments the treatment to which the sample has been subjected to lyse host cells does not lyse or only lyses a proportion of host mitochondria within said host cells. In certain embodiments, the proportion of host mitochondria that are not rendered permeable or which are left intact may be such that the amount of mtNA (e.g. mtDNA) is sufficient to interfere with or complicate downstream analysis (e.g. sequencing) of non-hose (e.g. pathogen) nucleic acid (NA) (e.g. non-host DNA) present in the sample. The amount of host mtNA that is sufficient to interfere with analysis of non-host NA will depend on, among other things, the amount of non-host NA present in the sample relative to the amount of host mtNA, the sensitivity of the analysis technique and the proportion of host mtNA lysed or otherwise removed during the initial cell lysis step. For example, as described in detail below, lysis of host cells using the cytolysin PLC was found to leave intact a proportion of host mtNA that was sufficient to impair the analysis of non-host NA present in the sample. Thus, a subsequent step to lyse or otherwise remove the mtNA improved the analysis of non-host NA in the sample.

In some embodiments the proportion of host mitochondria that are not rendered permeable or which are left intact by the treatment to which the sample has been subjected to lyse host cells may be in the range 0.1% to 99.9%. For example, the proportion may be 0.1%. 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%. That is to say the host cell lysis treatment may be relatively selective for lysis of the host cell while leaving a proportion, such as any proportion listed above, of the host mitochondria sufficiently intact that the mitochondrial nucleic acids remain within the mitochondria. In particular, the mitochondrial nucleic acids of said proportion of host mitochondria may therefore remain shielded from nucleases.

In some embodiments the treatment to which the sample has been subjected to lyse host cells is a treatment with a cytolysin. Cytolysin treatment was found to cause lysis of the host cells, but left host mitochondria relatively intact. In some embodiments the cytolysin comprises a phospholipase C.

In some embodiments the sample has, prior to said steps (a) and (b), been subjected to a treatment to deplete nucleic acid released from host cells within said sample or otherwise to render such nucleic acid in such a low quantity that it does not interfere with further downstream analysis, almost unidentifiable or unidentifiable. This is to say the optional step is performed.

In a second aspect method for depleting host nucleic acid in a biological sample, said sample having been previously obtained from an animal host, said method comprising the steps of:
 (a) lysing host cells contained in the sample;
 (b) carrying-out a process to physically deplete nucleic acid released from host cells within said sample or otherwise render such nucleic acid unidentifiable or in such low quantity that it does not interfere with downstream analysis of remaining nucleic acid;
 (c) depleting host mitochondria or host mitochondrial NA (mtNA) present in the sample; and
 (d) extracting and/or analysing remaining nucleic acid from the sample.

In some embodiments step (c) comprises depleting host mitochondrial DNA (mtDNA) and/or host mitochondrial RNA (mtRNA) present in the sample.

In some embodiments, step (b) is performed prior to step (c). In some embodiments, step (b) is performed concurrently with step (c), e.g. wherein the treatment to deplete nucleic acid released from host cells is the same treatment that is used to deplete host mitochondria or host mitochondrial NA (e.g. a single nuclease treatment that depletes both released host genomic DNA and mtNA). In some embodiments, step (b) is performed after step (c), for example nuclease treatment to deplete nucleic acid released from host cells may be employed following removal or lysis of host mitochondria.

In some embodiments step (a) comprises lysing at least 3%, 4%, 5%, 10%, 15%, 20%, 25%, 30%, 35%, 40%, 45%, 50%, 55%, 60%, 65%, 70%, 75%, 80%, 85%, 90% or at least 95% of the host cells in the sample.

In some embodiments step (a) does not lyse or only lyses a proportion of host mitochondria within said host cells. In some embodiments, the proportion is in the range 0.1% to 99.9%. For example, the proportion may be 0.1%. 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%.

In some embodiments lysing host cells present within the sample comprises adding a cytolysin to the sample. In particular, the cytolysin may be a phospholipase C.

In some embodiments optional step (b), i.e. carrying-out a process to physically deplete nucleic acid released from host cells within said sample or otherwise render such nucleic acid in such a low quantity that it does not interfere with further downstream analysis, almost unidentifiable or unidentifiable is carried out.

In some embodiments lysing said host cells comprises treating the sample with a cytolysin and/or a detergent. The detergent may comprise saponin, digitonin, Triton X-100, Nonidet, NP-40, Tween-20 and/or filipin.

In some embodiments in accordance with any aspect of the present invention the cytolysin may be a phospholipase, such as a phospholipase C. In particular, the cytolysin may be any cytolysin as disclosed in WO2018/109454, the cytolysin details of which, including amino acid sequences SEQ ID NOs: 1-5, are expressly incorporated herein by reference. A preferred cytolysin comprises the *Clostridium perfringens* phospholipase C (NCBI GenPept Accession No. EDT77687, version EDT77687.1, date: 10 Apr. 2008).

Said mitochondrial NA may be mtDNA or mtRNA.

In some embodiments in accordance with any aspect of the present invention wherein the sample is a blood sample, such as a human blood sample containing lymphocytes. The sample may further comprise or be suspected of comprising one or more microorganisms, e.g. unicellular organisms, such as a bacterial or fungal infection or one or more viruses.

In some embodiments in accordance with any aspect of the present invention wherein the animal host may have or be suspected of having a bacterial or fungal or viral infection. In particular, the method of the invention may be applied to a sample obtained from an animal (e.g. a human) having or suspected of having sepsis and for which identification of the underlying pathogen is required.

In some embodiments in accordance with any aspect of the present invention the method may result in at least a 2-fold, 5-fold, 10-fold, 20-fold, 30-fold, 40-fold or 50-fold depletion of host mitochondrial NA (e.g. mtDNA) originally contained within the sample.

In some embodiments in accordance with any aspect of the present invention the method may further comprise amplifying and/or purifying the remaining nucleic acid, optionally following a nucleic acid extraction step. The remaining nucleic acid may be enriched for, e.g., bacterial or fungal or viral nucleic acid (DNA or RNA).

In some embodiments in accordance with any aspect of the present invention the method may further comprise sequencing the remaining nucleic acid or the amplified product thereof, optionally following a nucleic acid extraction step. For example, bacterial, fungal or viral DNA or RNA (e.g. reverse transcribed to form cDNA) enriched relative to the original sample may be subjected to NGS analysis and sequence reads aligned with, e.g., microorganism reference genome(s) to identify the species and/or strain(s) of microorganisms present in the original sample. In some embodiments the sequencing covers at least 50% of at least one non-host genome with an average coverage or at least 3×. In particular embodiments, sequencing may be used to identify at least one drug resistance-conferring sequence in a pathogen present in the original sample. As is known to the skilled person, drug resistance (e.g. antibiotic resistance) may in some cases be conferred by mutation, presence or absence of specific genes and even by plasmids. Detection of any resistance-conferring sequence is, in principle, possible, e.g., by whole genome sequencing and sequence analysis.

Depletion of released nucleic acid in step (b), where present, may comprise physical depletion or virtual depletion, as described further herein. In some embodiments step (b), where present, may comprise treating the sample, after cell lysis, with a nuclease to deplete released nucleic acid, such as nuclear DNA, messenger RNA, etc. It is specifically contemplated herein that the sample may not be treated with a nuclease. For example, step (b) may be omitted because the released nucleic acid may be depleted during or as part of step (c). In particular, the method may comprise lysing host cells in the sample (e.g. with a cytolysin or a detergent), treating the sample with a detergent, such as saponin, to permeabilise host mitochondria, adding a nuclease to the sample to deplete released host nucleic acid (e.g. host nuclear DNA) and host mtDNA, and extracting and/or analysing (e.g. sequencing) remaining nucleic acid. In some embodiments, in particular where step (b) is present and comprises adding a nuclease, step (c) may comprise adding a detergent (as described above) to the previously-treated sample and allowing the previously added nuclease from step (b) to deplete mtNA. In some embodiments, step (c) may comprise adding further nuclease of the same type as that previously added in step (b) in order to deplete mtNA. In some embodiments, step (c) may comprise adding further nuclease of a different type from that previously added in step (b) in order to deplete mtNA.

The present inventors also contemplate studies in which host mitochondria nucleic acids are wanted, e.g. for sequencing analysis.

Accordingly, in a third aspect the present invention provides a method for isolating mitochondrial nucleic acids from a host cell-containing sample, comprising:
(a) lysing one or more host cells present in the sample (e.g. by adding a cytolysin, or an active variant thereof, to said sample);
(b) carrying-out a process to physically deplete nucleic acid released from host cells (e.g. host nuclear DNA) within said sample or otherwise render such nucleic acid unidentifiable; and
(c) extracting mitochondrial nucleic acids from the treated sample. In some embodiments, the method may further comprise amplifying and/or sequencing at least the mitochondrial nucleic acids (e.g. mtDNA).

In a fourth aspect the present invention provides a kit for use in a method of the invention, comprising:
i) a cytolysin, or an active variant thereof;
ii) a nuclease; and
iii) a detergent, a binding agent that selectively binds mitochondria, a DNA, RNA or PNA sequence that specifically hybridises to one or more sequences of the mitochondrial genome, or an sgRNA that selectively targets a RNA-guided DNA endonuclease enzyme, such as Cas9, to one or more sequences of the mitochondrial genome.

In some embodiments the detergent comprises saponin, digitonin, Triton-X100, nonidet, NP-40, Tween-20 and/or filipin.

In some embodiments the binding agent comprises an antibody, or binding fragment thereof, that selectively binds an outer mitochondrial membrane protein. In particular, the antibody, or binding fragment thereof, may selectively bind mitochondrial import receptor subunit TOM22 homolog (TOM22).

In some embodiments the DNA, RNA or PNA sequence (oligonucleotide) that specifically hybridises to one or more sequences of the mitochondrial genome may comprise a global mtDNA panel, such as the human representative global diversity panel described in Renaud et al., *Genome Biology* (2015) 16:224 and myBaits® Mito—Target Capture kit from Arbor Biosciences.

In some embodiments the sgRNA that selectively targets a RNA-guided DNA endonuclease enzyme (e.g. Cas9, Cas12, Cas13 or Cpf1) to one or more sequences of the mitochondrial genome may target sequences in the mitochondrial genome that encode mitochondrial enzymes, such as Cox1 or Cox3 (see Jo et al., *BioMed Research International*, 2015, Article ID 305716).

In some embodiments the cytolysin comprises a phospholipase C.

The cytolysin, nuclease, binding agent and/or detergent may be as described above in relation to the first or second aspect of the present invention.

The kit may be for use in a method in accordance with the first, second or third aspects of the present invention. The kit may further comprise suitable buffers and/or other reagents for performing the steps of the method of the first, second or third aspects of the present invention.

Embodiments of the present invention will now be described by way of examples and not limited thereby, with reference to the accompanying figures. However, various further aspects and embodiments of the present invention will be apparent to those skilled in the art in view of the present disclosure.

The present invention includes the combination of the aspects and preferred features described except where such a combination is clearly impermissible or is stated to be expressly avoided. These and further aspects and embodiments of the invention are described in further detail below and with reference to the accompanying examples and figures.

Figure 1:
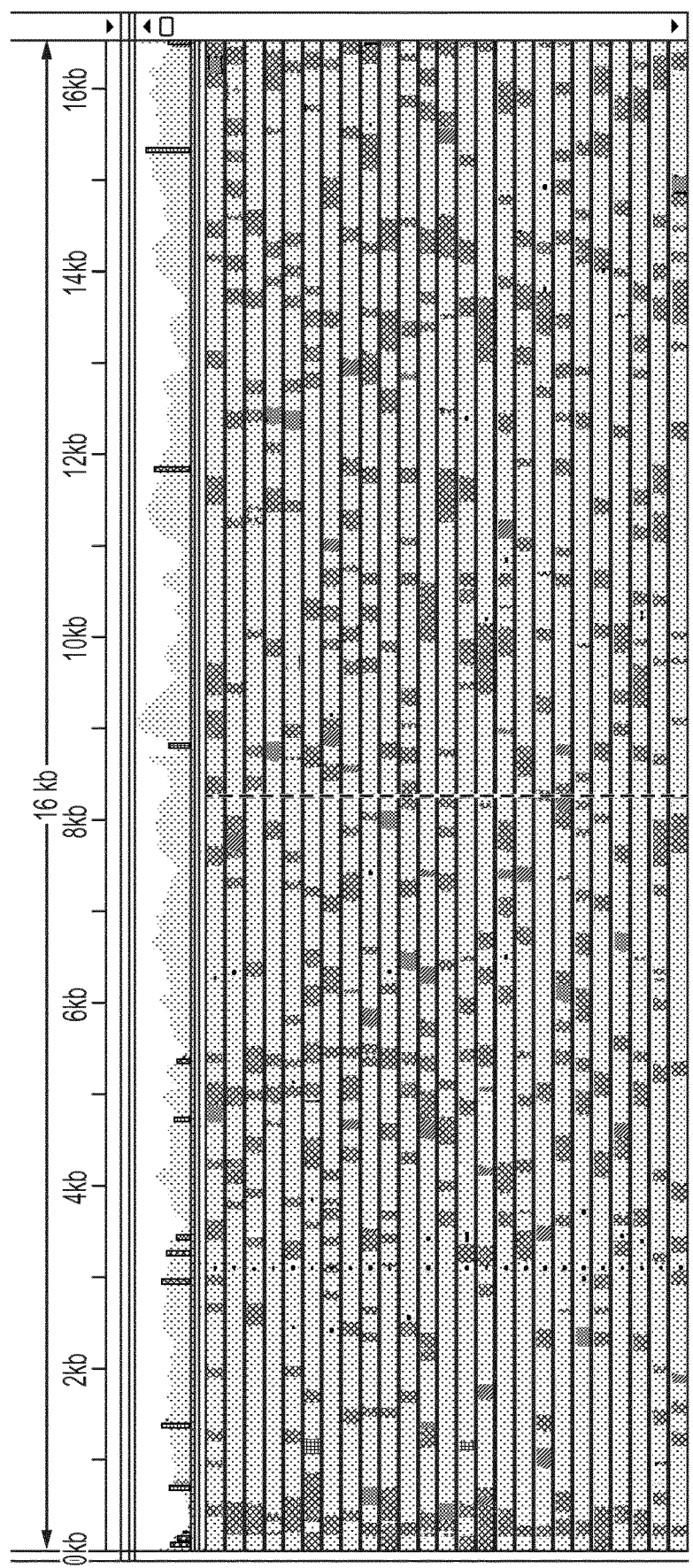
FIG. 1 shows a depiction of NGS sequence reads mapped to Chromosome M, being mitochondrial DNA. Broad coverage across the 16 kb mitochondrial genome is evident.

The Sequence Listing is submitted as an ASCII text file in the form of the file named Sequence_Listing.txt, which was created on Dec. 14, 2020, and is 19,199 bytes, which is incorporated by reference herein.

DETAILED DESCRIPTION OF THE INVENTION

In describing the present invention, the following terms will be employed, and are intended to be defined as indicated below.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

"Comprising" is intended to mean including the stated feature. Also contemplated are options wherein the terms "consisting of" or "consisting essentially of" are used instead of "comprising".

A "sample" as used herein may be a biological sample, such as a blood sample. Particular (e.g. clinical) samples of interest include bile, nail, nasal/bronchial lavage, bone marrow, stem cells derived from the body, bones, non-fetal products of conception, brain, breast milk, organs, pericardial fluid, buffy coat layer, platelets, cerebrospinal fluid, pleural fluid, cystic fluid, primary cell cultures, pus, saliva, skin, fetal tissue, fluid from cystic lesions, stomach contents, hair, teeth, tumour tissue, umbilical cord blood, mucus and stem cells. Particularly preferred samples include, though, joint aspirates, faeces, urine, sputum and, especially, blood (including plasma). Also contemplated herein tissue samples (e.g. a biopsy) and biological fluids other than blood, for example, a urine sample, a cervical smear, a cerebrospinal fluid sample, or a tumour or non-tumour tissue sample. It has been found that urine and cervical smears contains cells, and so may provide a suitable sample for use in accordance with the present invention. The sample may be one which has been freshly obtained from the subject (e.g. a blood draw) or may be one which has been processed and/or stored prior to making a determination (e.g. frozen, fixed or subjected to one or more purification, enrichment or extractions steps, including centrifugation). The sample may be derived from one or more of the above biological samples via a process of enrichment or amplification. A plurality of samples may be taken from a single patient, e.g. serially during a course of treatment (e.g. for an actual or suspected infection). Moreover, a plurality of samples may be taken from a plurality of patients. For the analysis of contamination, the sample may be an animal product (such as animal meat) having or suspected of having a contamination source (e.g. a microbial pathogen). A liquid sample might have a volume of between 10 µl and 100 ml, preferably between 10 µl and 50 ml, such as between 10 µl or 100 µl and 20 ml (e.g. 0.2 ml or 1 ml).

The animal host is preferably mammalian, e.g. a human, a domestic animal (e.g. a cow, sheep, horse or pig) or a companion animal (e.g. a dog or cat). Other vertebrate animal hosts are also contemplated herein, such as a bird or a fish. As used herein "host" is intended to encompass both an animal that harbours one or more non-host organisms (e.g. a microorganism) and an animal suspected of harbouring a non-host organism (e.g. suspected of being infected with a pathogen).

Cytolysin

A cytolysin (also known as a cytolytic toxin) is a protein secreted by a microorganism, plant, fungus or animal which is specifically toxic to a heterologous cell type(s), particularly promoting lysis of target cells. Preferred cytolysins are those secreted by microorganisms, particularly by bacteria, and/or those that are toxic to an animal (e.g. mammalian) cell type(s).

The cytolysin can be a cytolysin that has a detergent effect on the target cell membrane (e.g. a 26 amino acid delta toxin produced by *Staphylococcus*) or forms pores in the target cell membrane (e.g. Alpha hemolysin from *S. aureus*, Streptolysin O from *S. pyogenes*, and Perfringiolysin O produced by *C. perfringens*). See e.g.:

Alpha hemolysin from *S. aureus*—https://www.ncbi.nlm.nih.gov/protein/BBA23710.1 (SEQ ID No. 2):

```
  1 mktrivssvt ttlllgcilm npvanaadsd iniktgttdi gsnttvktgd lvtydkengm
 61 hkkvfysfid dknhnkkilv irtkgtiagq yrvyseegan ksglawpsaf kvqlqlpdne
121 vaqisdyypr nsidtkeyms tltygfngnv tgddsgkigg liganvsigh tlkyvqpdfk
181 tilesptdkk vgwkvifnnm vnqnwgpydr dswnpvygnq lfmktrngsm kaadnfldpn
241 kassllssgf spdfatvitm drkaskqqtn idviyervrd dyqlywtstn wkgtntkdkw
301 tdrsseryki dwekeemtn
```

Streptolysin O from *S. Pyogenes*—https://www.ncbi.nlm.nih.gov/protein/BAD77794.2 (SEQ ID No. 3):

```
  1 msnkktfkky srvaglltaa liignlvtan aesnkqntas tettttseqp kpesseltie
 61 kagqkmddml nsndmiklap kemplesaek eekksedkkk seedhteein dkiyslnyne
121 levlaknget ienfvpkegv kkadkfivie rkkkninttp vdisiidsvt drtypaalql
181 ankgftenkp davvtkrnpq kihidlpgmg dkatvevndp tyanvstaid nlvnqwhdny
241 sggntlpart qytesmvysk sqieaalnvn skildgtlgi dfksiskgek kvmiaaykqi
301 fytvsanlpn npadvfdksv tfkdlqrkgv sneapplfvs nvaygrtvfv kletssksnd
361 veaafsaalk gtdvktngky sdilenssft avvlggdaae hnkvvtkdfd virnvikdna
421 tfsrknpayp isytsvflkn nkiagvnnrt eyvettstey tsgkinlshq gayvaqyeil
481 wdeinyddkg kevitkrrwd nnwysktspf stviplgans rnirimarec tglawewwrk
541 viderdvkls keinvnisgs tlspygsity k
```

Preferably, the cytolysin is a cytolysin that digests a cell membrane component, (e.g. phospholipids, i.e. is a phospholipase). An example is Sphingomylinease (also known as beta-toxin) from *S. aureus*, see e.g. https://www.ncbi.nlm.nih.gov/protein/CAA43885.1 (SEQ ID No. 4):

```
  1 mmvkktksns lkkvatlala nlllvgaltd nsakaeskkd dtdlklvshn vymlstvlyp
 61 nwgqykradl igqssyiknn dvvifneafd ngasdkllsn vkkeypyqtp vlgrsqsgwd
121 ktegsysstv aedggvaivs kypikekigh vfksgcgfdn dsnkgfvytk iekngknvhv
181 igthtqseds rcgaghdrki raeqmkeisd fvkkknipkd etvyiggdln vnkgtpefkd
241 mlknlnvndv lyaghnstwd pqsnsiakyn ypngkpehld yiftdkdhkq pkqlvnevvt
301 ekpkpwdvya fpyyyvyndf sdhypikays k
```

The phospholipase can be a phospholipase A, B, C or D, such as PLD from *Streptomyces*, see e.g. https://www.ncbi.nlm.nih.gov/protein/BAL15170.1 (*Streptomyces vinaceus*) (SEQ ID No. 5):

```
  1 mhrhtpslrr psahlpsala vraavpaall alfaavpasa apaagsgadp aphldaveqt 61 lrqvspgleg qvwertagnv ldastpggad wllqtpgcwg ddkctarpgt eqllskmtqn 121 isqatrtvdi stlapfpnga fqdaivsglk tsaargnklk vrvlvgaapv yhlnvlpsky 181 rdelvaklga darnvdlnva smttsktafs wnhskllvvd gqsvitggin dwkddyleta 241 hpvadvdlal rgpaaasagr yldelwswtc qnksniasvw fassngaacm pamakdtapa 301 apapapgdvp avavgglgvg ikrndpsssf rpalpsapdt kcvvglhdnt nadrdydtvn 361 peesalrtli ssanrhieis qqdvnatcpp lprydirvyd alaarmaagv kvrivvsdpa 421 nrgavgsggy sqikslseis dtlrdrlalv tgdqgaakat mcsnlqlatf rssqsptwad 481 ghpyaqhhkv vsvddsafyi gsknlypawl qdfgyvvesp aaaaqlnarl lapqwqysra 541 tatidheral cqs
```

Preferably the phospholipase is a phospholipase C (PLC) (i.e. a phospholipase that cleaves before the phosphate, releasing diacylglycerol and a phosphate-containing head group). Preferably the PLC is a bacterial PLC, selected from any of the following groups:

Group 1—Zinc metallophospholipases

Group 2—Sphingomyelinases (e.g. sphingomyelinase C)

Group 3—Phosphatidylinositol

Group 4—Pseudomonad PLC

A Group 1 PLC is preferred, particularly PLC from *Clostridium perfringens*, see e.g. https://www.ncbi.nlm.nih.gov/protein/EDT77687.1 (SEQ ID No.1):

```
  1 mkrkickali caalatslwa gastkvyawd gkidgtgtha mivtqgvsil endmsknepe 61 svrknleilk enmhelqlgs typdydknay dlyqdhfwdp dtdnnfskdn swylaysipd 121 tgesqirkfs alaryewqrg nykqatfylg eamhyfgdid tpyhpanvta vdsaghvkfe 181 tfaeerkegy kintagcktn edfyadilkn kdfnawskey argfaktgks iyyshasmsh 241 swddwdyaak vtlansqkgt agyiyrflhd vsegndpsvg knvkelvayi stsgekdagt 301 ddymyfgikt kdgktqewem dnpgndfmtg skdtytfklk denlkiddiq nmwirkrkyt 361 afpdaykpen ikviangkvv vdkdinewis gnstynik
```

This cytolysin provides for highly effective lysis of animal host cells in the present technology, despite reports in the literature that purified *C. perfringens* PLC when used alone has no cytotoxic activity against leukocytes.

The cytolysin can be a wild-type cytolysin or an active variant (produced e.g. by recombinant DNA technology). An active variant of a cytolysin is a variant of a cytolysin that retains the ability to lyse a target cell, demonstrating e.g. at least 10%, preferably at least 25%, preferably at least 50%, preferably at least 60%, preferably at least 70%, preferably at least 80%, preferably at least 90%, preferably at least 95% of the activity of the wild-type protein in any assay where lytic activity against a target cell can be shown for the wild-type protein.

"An active variant thereof" includes within its scope a fragment of the wild-type protein. In preferred embodiments, a fragment of the wild-type protein is selected that is at least 10% of the length of the wild-type protein sequence, preferably at least 20%, preferably at least 30%, preferably at least 40%, preferably at least 50%, preferably at least 60%, preferably at least 70%, preferably at least 80%, preferably at least 90% and most preferably at least 95% of the length of the wild-type protein sequence.

"An active variant thereof" also includes within its scope a protein sequence that has homology with the wild-type protein sequence, such as at least 50% identity, preferably at least 60%, preferably at least 70%, preferably at least 80%, preferably at least 85%, preferably at least 90%, preferably at least 95%, preferably at least 97%, and most preferably at least 99% identity, for example over the full wild-type sequence or over a region of contiguous amino acid residues representing 10% of the length of the wild-type protein sequence, preferably at least 20%, preferably at least 30%, preferably at least 40%, preferably at least 50%, preferably at least 60%, preferably at least 70%, preferably at least 80%, preferably at least 90% and most preferably at least 95% of the length of the wild-type protein sequence. Methods of measuring protein homology are well known in the art and it will be understood by those of skill in the art that in the present context, homology is calculated on the basis of amino acid identity (sometimes referred to as "hard homology").

The homologous active cytolysin variant typically differs from the wild-type protein sequence by substitution, insertion or deletion, for example from 1, 2, 3, 4, 5 to 8 or more substitutions, deletions or insertions. The substitutions are preferably 'conservative', that is to say that an amino acid may be substituted with a similar amino acid, whereby similar amino acids share one of the following groups: aromatic residues (F/H/W/Y), non-polar aliphatic residues (G/A/P/I/L/V), polar-uncharged aliphatics (C/S/T/M/N/Q) and polar-charged aliphatics (D/E/K/R). Preferred subgroups comprise: G/A/P; I/L/V; C/S/T/M; N/Q; D/E; and K/R.

The cytolysin or active variant (as described above) may have any number of amino acid residues added to the N-terminus and/or the C-terminus provided that the protein retains lytic activity.

Preferably, no more than 300 amino acid residues are added to either or both ends, more preferably no more than 200 amino acid residues, preferably no more than 150 amino acid residues, preferably no more than 100 amino acid residues, preferably no more than 80, 60 or 40 amino acid residues, most preferably no more than 20 or 10 or 5 amino acid residues.

Preferably, the sample is subject to mixing after the cytolysin has been added.

Preferably, to promote cytolysin activity, particular buffering conditions and/or incubation temperature might be provided for any one selected cytolysin. Cytolysin incubation can take place at e.g. between 5° C. and 50° C., such as between 15° C. and 45° C. (e.g. 37° C.), and for between 1 min and 120 min, preferably between 1 min and 60 min, more preferably between 1 min and 30 min (e.g. 15 min or 20 min). For part or all of the cytolysin incubation, the sample is preferably subject to mixing/shaking, at e.g. between 1 and 1500 rpm, preferably between 1 and 1000 rpm (e.g. at 500 rpm or 1000 rpm).

Preferably, the cytolysin is used in the sample at a concentration of at least 0.1 mg/ml, such as between 0.1 mg/ml and 100 mg/ml, preferably between 0.1 mg/ml and 100 mg/ml, preferably between 0.1 mg/ml and 50 mg/ml (e.g. at 4 mg/ml).

Nuclease

If a nuclease (e.g. a DNase) is used in the present methodology, the nuclease (e.g DNase) can be an endonuclease or an exonuclease (or a combination thereof can be provided), preferably an endonuclease.

Preferred nucleases (particularly where the biological sample is a blood sample) include HL-SAN nuclease (heat labile salt activated nuclease, supplied by Arcticzymes) and MolDNase (endonuclease active in the presence of chaotropic agents and/or surfactants, supplied by Molzym), and active variants are also contemplated, essentially as discussed above in relation to the cytolysin.

Preferably, the sample is subject to mixing after the nuclease has been added.

Preferably, to promote nuclease activity, particular buffering conditions and/or incubation temperature might be provided for any one selected nuclease. Nuclease incubation can take place at e.g. between 5° C. and 50° C., such as between 15° C. and 45° C. (e.g. 37° C.), and for between 1 min and 120 min, preferably between 1 min and 60 min, more preferably between 1 min and 30 min (e.g. 15 min). In particularly preferred embodiments, the DNase buffer is added to the sample, containing the cytolysin, and incubated (e.g. as described above) before pelleting. The pellet is then resuspended in DNase buffer and the nuclease (e.g. DNase0 itself is added (ahead of further incubation).

In embodiments where a nuclease is employed to deplete released nucleic acid (e.g. nuclear DNA) and is also employed to deplete mtNA following mitochondrial permeabilisation (e.g. with a detergent such as saponin), preferably, the same nuclease used in each case (i.e. to digest released host nuclear DNA and to digest mtNA released after, e.g., detergent treatment). However, it is specifically contemplated herein that the nuclease for nuclear DNA depletion and mtNA depletion may differ. In certain embodiments, a single nuclease treatment step is performed after both cell lysis and mitochondrial permeabilisation have been carried out.

Host Nucleic Acid Depletion

Host nucleic acid depletion, such as depletion of nuclear DNA and/or RNA (e.g. mRNA) depletion may have been carried out prior to host mitochondrial depletion and/or host mtNA depletion in accordance with the first aspect of the invention or may be carried out as part of the method in accordance with the second aspect of the invention.

Lysis of one or more host cells present in the sample is effected. This may involve addition of a cytolysin or a detergent that causes (selective) lysis of the host cells, releasing host nucleic acid such that it can be (partially or completely) depleted. Nucleic acid within a non-host cell or particle (e.g. pathogen) is essentially left intact (i.e. has not been significantly removed from the sample or digested) and identifiable, such that it can be subsequently collected and analysed and, in particular, identified (by e.g. sequencing or targeted PCR). A nucleic acid is identifiable e.g. if its sequence and/or biological origin can be ascertained. Preferably, therefore, the cytolysin is added to the sample and allowed to act for a period of time such that sufficient host cell lysis can occur.

The method of depleting host nucleic acid contemplates both physical depletion and (in the context of the present technology) virtual depletion (of nucleic acid released from host cells within the sample). Physical depletion can involve e.g. digesting the nucleic acid (i.e. breaking down nucleic acid polymers to e.g. base monomers) or removing nucleic acid from the sample (e.g. by any nucleic acid capture method known to the skilled person, such as deploying nucleic acid-binding magnetic beads in the sample to bind DNA and/or RNA, which can subsequently be removed or harvested from the sample).

Virtual depletion involves rendering (released) nucleic acid unidentifiable (via, in particular, targeted PCR or, most preferably, sequencing). For DNA, this means rendering the DNA non-amplifiable (e.g. by PCR) and/or (preferably) non-sequenceable. For RNA, this means rendering the RNA non-amplifiable, non-reverse-transcribable and/or (preferably) non-sequenceable. A preferred process for such rendering (particularly for DNA) involves adding a photoreactive nucleic acid-binding dye, such as propidium monoazide (PMA) or ethidium monoazide (EMA), to the sample and inducing photoreaction.

Most preferably, however, the method of depletion is via digestion of nucleic acid, most preferably via enzymatic digestion. Preferably, a nuclease is added to the sample and allowed to act for a period of time such that sufficient nucleic acid digestion can occur. Preferably, therefore, a nuclease (e.g. a deoxyribonuclease (DNase) and/or a ribonuclease (RNase)) is added to the sample (and preferably allowed to act for a period of time such that sufficient DNA/RNA digestion can occur). The nuclease can have both DNase and RNase activity (e.g. HL-SAN DNase). Depletion of host DNA is important if analysis of non-host (e.g. pathogen) DNA is to be carried out. Depletion of host RNA is important if analysis of non-host (e.g. pathogen) RNA is to be carried out, and indeed can facilitate the optimisation of DNA analysis (e.g. DNA sequencing).

In such embodiments, the method preferably further comprises the subsequent step of neutralising the (or each) nuclease (i.e. decreasing or substantially eliminating the activity of the nuclease). The skilled person will recognise a range of neutralisation options, to be selected for each depletion protocol. This might include heat inactivation or, preferably, buffer exchange (i.e. the removal of a buffer in which the nuclease is active and/or replacement with or addition of a buffer in which the nuclease is substantially inactive). Optionally, the temperature of the sample (at any/all stage(s) at/before extraction of remaining nucleic acid from the sample) is maintained at 65° C. or less, 50° C. or less, preferably 45° C. or less, preferably 40° C. or less, to optimise subsequent release of nucleic acid from the pathogen (particularly from bacterial cells).

Host Mitochondrial Depletion

Depletion of host mitochondrial nucleic acids (mtNA) further enriches the non-host nucleic acid fraction of the sample and further enhances detection of non-host DNA and/or RNA by reducing the host NA "background".

Host mtNA depletion comprises direct depletion of host mitochondria, for example, using techniques that capture or otherwise isolate substantially intact host mitochondria from the sample. One example of this approach is the use of a specific binding agent (e.g. antibody) that selectively binds an outer mitochondrial membrane protein, e.g. Mitochondrial import receptor subunit TOM22 homolog (TOM22).

Alternatively or additionally, host mtNA depletion may comprise adding a detergent (e.g. saponin, digitonin, Triton X-100, nonidet, NP-40, Tween-20 or filipin) to the sample to render host mitochondria more permeable and thereby facilitate the action of a nuclease to digest mtNA. As shown in Example 7 and Table 11, this approach resulted in a very high degree of enrichment of pathogen DNA due to efficient depletion of both human nuclear DNA and human mtDNA.

Alternatively or additionally, host mtNA depletion may comprise extraction of whole nucleic acids and further, targeted removal of the host mtNA from the pool of released or extracted nucleic acid. The human mtDNA genome is around 16 kb and so is amenable to capture and targeted removal techniques that may be infeasible for removal of the entire human nuclear genome. Therefore the present inventors specifically contemplate that, having depleted at least the host nuclear DNA, the mtDNA may be depleted from a mixed pool containing both host mtDNA and non-host nucleic acid by use of a library capture approach and/or a a RNA-guided DNA endonuclease enzyme, such as Cas9, -targeted approach.

Library capture of mitochondrial DNA may comprise a step of contacting the released nucleic acid with a panel of DNA and/or RNA and/or PNA baits (e.g. immobilised oligonucleotide probes) that target (i.e. hybridise to) sequences in the host mitochondrial genome. In this way mtDNA is captured and removed from the sample providing for relative enrichment of pathogen or other microbial or viral nucleic acid. Commercial capture libraries for mtDNA are available (e.g. xGen® Human mtDNA Research Panel v1.0 from IDT, and myBaits® Mito—Target Capture kit from Arbor Biosciences). Although these libraries are designed to enrich the sample in mtDNA, in our approach the use of this type of capture panel may be used for depleting mtDNA. Instead of working with captured DNA, our method, in certain embodiments, works with the non-captured content.

In a RNA-guided DNA endonuclease enzyme like CRISPR associated protein 9 (Cas9)-mediated approach to mtDNA depletion, binding of host mitochondrial DNA uses a guide RNA (e.g. sgRNA) that targets Cas9 to a host mitochondrial DNA target sequence. In particular embodiments, the Cas9 may be inactive. In these embodiments, the inactive Cas9 is targeted to the mtDNA via appropriate guide RNA and the Cas9-mtDNA complex is selectively removed by virtue of a Cas9-specific binding agent.

In an alternative embodiment, an RNA-guided DNA endonuclease enzyme such as CRISPR associated protein 9 (Cas9)-mediated approach may be employed for mtDNA depletion, cleavage of host mitochondrial DNA is achieved using a single guide RNA (sgRNA) that targets a host mitochondrial DNA target sequence. In particular embodiments, the extracted nucleic acid (NA) is fragmented and specific sequences (adaptors) are added to the ends (i.e. 5' and 3' ends) of the fragmented NAs by ligation or using a transposase. In these embodiments, the Cas9 is targeted to the mtDNA via appropriate sgRNA and the mtDNA sequence is cleaved. The resulting NAs are amplified by for example PCR using primers hybridizing to the adaptor sequences. The cleaved NAs lack an adaptor at both ends, and so are not amplified and, therefore, the mtDNA proportion is reduced. An example of this approach for depleting target sequences has been described by Gu et al., *Genome Biology* (2016) 17:41

Further Steps

In preferred embodiments, the method further comprises the step of (optionally extracting) analysing remaining (preferably non-host) nucleic acid from the sample (or aliquot thereof). Part or all of the remaining nucleic acid (particularly non-host nucleic acid) will be intact and identifiable. The non-host nucleic acid will have been enriched relative to the original sample by complete or partial depletion of host nucleic acid, including host nuclear DNA and host mtNA.

Typically, the extraction process, where used, will involve a centrifugation step to collect, in particular, non-host cells/particles (e.g. pathogens) (virus particles and/or, in particular, bacterial and/or non-animal (e.g. non-mammalian) (e.g. unicellular) eukaryotic cells, such as fungi), from which the nucleic acid can be obtained. The bacterial or other microbial cells may be, but need not be, pathogenic. In particular, analysis of non-pathogenic microbiota is specifically contemplated herein. The human microbiota include bacteria, archaea, fungi, protists and viruses. Exemplary microbiota include those identified in the Human Microbiome Project (see, e.g., The Human Microbiome Project Consortium, *Nature,* 2012, Vol. 486, pp. 215-221). Centrifugation conditions can be selected such that bacterial and non-animal cells, but not virus particles, are pelleted, or such that virus particles are pelleted in addition to bacterial and non-animal cells. If the former, standard virus detection tests could be performed on the supernatant.

Nucleic acid can be obtained from the pathogen(s) or other microorganisms using methods known in the art, and might involve the addition of a lysis buffer, a lytic enzyme(s) (degrading or abrogating cell membranes, cell walls and/or viral capsids), and/or a protease, e.g. proteinase K. Preferred lytic enzymes include lysozyme, mutanolysin, lysostaphin, chitinase and lyticase.

Optionally, the extracted nucleic acid (or aliquot thereof) is subject to a purification process, such as one known in the art. During purification of DNA, RNase is optionally used to facilitate the optimisation of subsequent DNA sequencing. However, RNase is omitted from any purification step if non-host (e.g. pathogen) RNA extraction is of interest (for e.g. subsequent RNA sequencing) (and a DNase might be used to assist with purification).

In preferred embodiments, extracted nucleic acid (or aliquot thereof) is subject to an amplification process, such as whole genome amplification, to increase the copy number of the nucleic acid, particularly where the biological sample is a blood sample.

For RNA, this might involve direct amplification or conversion of RNA to cDNA, followed by amplification of cDNA.

In preferred embodiments, the method further comprises the step of conducting a nucleic acid amplification test (e.g. targeted PCR amplification process, isothermal amplification, nucleic acid sequence-based amplification (NASBA)) on the extracted nucleic acid (RNA, DNA or cDNA) (or aliquot thereof) or, preferably, conducting a sequencing process on the extracted nucleic acid (or aliquot thereof), such as (e.g. short or long read) DNA or RNA sequencing, using e.g. nanopore or Illumina® sequencing.

In the preceding embodiments, nucleic acid (particularly host nucleic acid) previously rendered unidentifiable will not be amplified by any amplification process and/or (in particular) sequenced by any sequencing process.

In comparison with methods of the prior art (e.g. the MolYsis® technique, which deploys chaotropic agents to lyse host cells prior to host nucleic acid digestion), the method of the present invention facilitates highly improved depletion of host nucleic acid (particularly DNA and/or RNA, including mtDNA and/or mtRNA), while leaving non-host (e.g. pathogen, particularly bacterial) nucleic acid intact (and identifiable), leading to highly improved non-host (e.g. pathogen) nucleic acid enrichment, sufficient for subsequent sequencing-based (e.g. next-generation sequencing [NGS] based) (e.g. pathogen) diagnostics. A key factor in this advance has been the ability to achieve e.g. a $5 \times 10^4$ or greater, such as $10^5$ or greater (e.g. $10^6$ or greater), fold depletion of host DNA (and host mtDNA) from within biological sample from a mammalian host, and these are preferable outcome features of the present technology (as is a fold depletion of 10 or greater, $10^2$ or greater, $10^3$ or greater, $5 \times 10^3$ or greater, or $10^4$ or greater). It is particularly preferred that host nucleic acid (e.g. DNA and mtDNA) is undetectable or substantially depleted (e.g. undetectable or detectable only at a low level via qPCR) following deployment of the method of the invention. In more general terms, the selective depletion of host nucleic acid, including host mtNA enables enrichment of non-host nucleic acid, and hence improved identification of non-host organisms. This technology is thus applicable to fields other than medical microbiology, such as biological research, veterinary medicine/diagnostic, and agriculture/food safety.

The following is presented by way of example and is not to be construed as a limitation to the scope of the claims.

EXAMPLES

Materials and Methods

Saponin was obtained from Tokyo Chemical Industry (catalog No. S0019; CAS number 8047-15-2). Sapogenein content ca. 10%, pH 4.0-7.0 (at 5% aqueous solution).

Phospholipase C (PLC) was obtained from Sigma with the reference P7633-500UN: Phospholipase C from *Clostridium perfringens* (*C. welchii*) Type I, lyophilized powder, 10-50 units/mg protein; CAS Number: 9001-86-9; EC Number: 232-638-2.

Protocol for Human NA Depletion by PLC+Nuclease+Anti-TOM22 MACS Kit

1. Spike whole blood (200 μl) with *Escherichia coli, Candida albicans* or *Staphylococcus aureus* at desired concentration. Non-spiked blood is used as control
2. Add 20 μl of PLC (0.04 mg/μl)
3. Vortex 10 seconds
4. Incubate 15 min at 37° C. at 1000 rpm
5. Add 200 μl of HL-SAN buffer (5M NaCl, 100 mM MgCl2)
6. Add 10 μl of HL-SAN nuclease (25 U/μl)
7. Vortex 10 seconds
8. Incubate 15 min at 37° C. at 1000 rpm
9. Add 1.4 ml of PBS
10. Centrifuge 10 min at 12,000 g and discard supernatant
11. Add 700 μl pf PBS and resuspend the pellet by pipetting up and down
12. Add additional 700 μl of PBS
13. Centrifuge 10 min at 12,000 g and discard supernatant
14. Add 200 μl pf PBS and resuspend the pellet by pipetting up and down Mitochondrial Immunodepletion by Anti-Tom22 Ab To deplete mitochondria, the Isolation kit human (MACS Miltenyi Biotec) was used following the adapted protocol as described below.

1. Add 750 μl of ice-cold 1× separation buffer (included in the kit) to the resuspended pellet and mix
2. Add 50 μl of microbeads anti-ToM22
3. Mix well and incubate 1 hour 4° C. with gentle agitation
4. Just before finishing the incubation, prepare a MS column by loading 500 μl of 1× separation buffer
5. Load the mixture of sample plus beads into the column (sited in the MiniMAC separator) and collect the eluate. This fraction is the enriched sample
6. (Optionally) Wash the column with 1 ml of separation buffer 7. (Optionally) Add 1 ml to the column, retire the column from the separator and extract the content by flushing the column with the emboli. Collecting the content in a separate tube (mitochondrial fraction)
8. Extract nucleic acid (NA) with EasyMAg extraction robot (Biomerieux) standard protocol; select "blood" as matrix and elute in 40 µl of elution buffer Evaluation of Mitochondrial Depletion by Cytometer To check depletion efficiency, all the fractions obtained during the immunodepletion (before extracting them) were analyzed by FACS. Only one population was present, so the number of events in a determined time were compared among the fractions.

Evaluation of Mitochondrial Depletion by qPCR

To check depletion efficiency, qPCR was carried out using specific Taqman probes (Hs00537670_s1 and Hs02596867_s1) for human DNA and mtDNA, respectively, as well as for each pathogen tested. Ct were compared.

Protocol for Human NA Depletion by PLC+Nuclease+Saponin+Nuclease

1. Spike whole blood (200 µl) with *Escherichia coli*, *Candida albicans* or *Staphylococcus aureus* at desired concentration. Non-spiked blood is used as control
2. Add 20 µl of PLC (0.04 mg/µl)
3. Vortex 10 seconds
4. Incubate 15 min at 37° C. at 1000 rpm
5. Add 200 µl of HL-SAN buffer (5M NaCl, 100 mM MgCl2)
6. Add 10 µl of HL-SAN nuclease (25 U/µl)
7. Vortex 10 seconds
8. Incubate 15 min at 37° C. at 1000 rpm
9. Add 1.4 ml of PBS
10. Centrifuge 10 min at 12,000 g and discard supernatant
11. Add 700 µl pf PBS and resuspend the pellet by pipetting up and down
12. Add additional 700 µl of PBS
13. Centrifuge 10 min at 12,000 g and discard supernatant
14. Add 200 µl pf PBS and resuspend the pellet by pipetting up and down
15. Add 200 µl of 1% Saponin
16. Vortex 10 seconds
17. Incubate 10 min at RT
18. Add 350 µl of water and wait 30 seconds
19. Add 12 µl of 5M NaCl
20. Centrifuge 5 min at 12,000 g and discard supernatant
21. Add 200 µl of PBS and resuspend the pellet by pipetting up and down
22. Add 200 µl of HL-SAN buffer (5M NaCl, 100 mM MgCl2)
23. Add 10 µl of HL-SAN nuclease (25 U/µl)
24. Vortex 10 seconds
25. Incubate 15 min at 37° C. at 1000 rpm
26. Add 1.4 ml of PBS
27. Centrifuge 10 min at 12,000 g and discard supernatant
28. Add 700 µl pf PBS and resuspend the pellet by pipetting up and down
29. Add additional 700 µl of PBS
30. Centrifuge 10 min at 12,000 g and discard supernatant
31. Resuspend in 200 µl of PBS
32. Extract NA with EasyMAg extraction robot (Biomerieux) standard protocol; select "blood" as matrix and elute in 40 µl of elution buffer
33. Amplify 4 µl of extracted DNA by Whole genome amplification (WGA) using Repli-g single cell kit (Qiagen) following manufacturer's instructions
34. Purify whole genome amplified samples with Ampure XP beads (Agencourt) at ratio 1:1 and elute with 40 µl of water
35. Quantify the dsDNA in the samples with Qubit fluorometer Library Preparation: MinION 1. Treat 1 µg of dsDNA with T7 endonuclease (NEB):
   Add 2 µl of 10× reaction buffer
   Add 1 µl of T7 endonuclease
   Add water until 20 µl
   Mix by flicking and spin
   Incubate 15 min at 37° C.
2. Purify T7 treated samples with Ampure XP beads (Agencourt) at ratio 1:1.8 (sample: beads) and elute with 24 µl of water
3. Prepare the T7-treated DNA for being sequenced with the SQK-RLB001: Rapid Low Input by PCR Barcoding kit (ONT) following manufacturer's instructions
4. Load the sample (or pool of samples if several samples have been prepared) in a 9.4 or 9.5 flow cell inserted in the MinION following ONT instructions
5. Connect the MinION to the MinKNOW software and start the run selecting SQK-RLB001 kit and "live" basecalling
6. The resulting fastqs are analyzed by the EPI2ME software using WIMP program (ONT) and the % of target reads are calculated comparing the specific target reads with Total reads (including classified+non classified reads). To calculate the % of human reads, both WIMP software and alignment of the fastq to Hg38 using Minimap program were carried out. The % of reads aligned to mitochondria were calculated by comparing ChrM mapped reads to the Hg38 mapped reads.

Library Preparation: MiSeq

1. Calculate the volume to start with 1.5 ng of dsDNA in 5 µl. Prepare the library using Nextera XT kit (Illumines®) following manufacturer's instructions
2. Quantify the library and dilute it to 4 nM. Denature 5 µl of 4 nM library or pool of libraries if more than 1 sample has been prepared.
3. Load the library in the MiSeq cartridge (i.e. 300 cycles v2) and start the run following Illumina® instructions
4. The resulting fastq is trimmed to eliminate adapters, short reads (<40 nt) and low quality reads and nucleotides. The trimmed fastq is aligned to the specific target reference and to the Hg38 (to calculate human and mitochondrial content) using Bowtie2. The number of mapped reads is calculated by loading the resulting .bam file in the Qualimap program. The % of target reads is calculated by comparing mapped reads to the total.

Protocol for Human NA Depletion by PLC+Nuclease+Extraction+Library Capture

1. Spike whole blood (200 µl) with *Escherichia coli*, *Candida albicans* or *Staphylococcus aureus* at desired concentration. Non-spiked blood is used as control
2. Add 20 µl of PLC (0.04 mg/µl)
3. Vortex 10 seconds
4. Incubate 15 min at 37° C. at 1000 rpm
5. Add 200 µl of HL-SAN buffer (5M NaCl, 100 mM MgCl2)
6. Add 10 µl of HL-SAN nuclease (25 U/µl)
7. Vortex 10 seconds
8. Incubate 15 min at 37° C. at 1000 rpm
9. Add 1.4 ml of PBS
10. Centrifuge 10 min at 12,000 g and discard supernatant 11. Add 700 µl pf PBS and resuspend the pellet by pipetting up and down
12. Add additional 700 µl of PBS
13. Centrifuge 10 min at 12,000 g and discard supernatant
14. Add 200 µl pf PBS and resuspend the pellet by pipetting up and down
15. Extract NA with EasyMAg extraction robot (Biomerieux) standard protocol; select "blood" as matrix and elute in 40 µl of elution buffer
16. Amplify 4 µl of extracted DNA by Whole genome amplification (WGA) using Repli-g single cell kit (Qiagen) following manufacturer's instructions
17. Purify whole genome amplified samples with Ampure XP beads (Agencourt) at ratio 1:1 and elute with 40 µl of water
18. Quantify the dsDNA in the samples with Qubit fluorometer
19. Prepare a library to be sequenced in MiSeq by using the kit Nextera (Illumine). According to the quantification, start with 50 ng of dsDNA and follow manufacturer instructions.
20. Once the library is prepared, quantify it by Qubit
21. Library capture could be carried out by using myBaits® Mito-Target Capture kit from Arbor Biosciences or by using xGen® Human mtDNA Research Panel v1.0 from IDT, by following manufacturer's instructions, taking into account that the library has been prepared with Nextera kit and select the corresponding manufacturer protocol. In the case of xGen the Cot-1 DNA addition should be omitted.
22. For both library captures the starting amount of DNA is 500 ng and the method has to be disrupted after the binding of hybridization mixture with magnetic beads. Once the hybridization is finished, magnetic beads (Streptavidine beads in case of xGen) are added to the hybridization reaction, mixed and incubated together to allow the binding of magnetic beads to capture probes (in case of xGEN the probes are labelled with biotin and bind to the streptavidine of the magnetic beads).
23. The mixture is placed in a magnetic rack and the beads are pelleted. The supernatant is collected.
24. The collected supernatant is purified to eliminate the blocking probes and all the reagents of the sample by Ampure XP beads (Agencourt) at ratio 1:1.5 (sample:beads) and elute with 25 µl of water.
25. Amplify the purified DNA by using P5 and P7 primers (Illumina)
26. Purify the PCR with Ampure XP beads (Agencourt) at ratio 1:1.8 (sample:beads) and elute with 25 µl of water.
27. Quantify the library and dilute it to 4 nM. Denature 5 µl of 4 nM library or pool of libraries if more than 1 sample has been prepared.
28. Load the library in the MiSeq cartridge (i.e. 300 cycles v2) and start the run following Illumina® instructions
29. The resulting fastq is trimmed to eliminate adapters, short reads (<40 nt) and low quality reads and nucleotides. The trimmed fastq is aligned to the specific target reference and to the Hg38 (to calculate human and mitochondrial content) using Bowtie2. The number of mapped reads is calculated by loading the resulting .bam file in the Qualimap program. The % of target reads is calculated by comparing mapped reads to the total.

Protocol for Human NA Depletion by PLC+Nuclease+Extraction+Cas9 Cleavage
1. This protocol is similar to the previous one till step 20.
2. Once the library is prepared and quantified by Qubit, the library is treated with Cas9. For example with Cas9 Nuclease, *S. pyogenes* (M0386) from New England Biolabs (NEB) using sgRNAs containing specific mtDNA region.
3. The treated sample is amplified using P5 and P7 primers (Illumina)
4. Purify the PCR with Ampure XP beads (Agencourt) at ratio 1:1.8 (sample:beads) and elute with 25 µl of water.
5. Quantify the library and dilute it to 4 nM. Denature 5 µl of 4 nM library or pool of libraries if more than 1 sample has been prepared.
6. Load the library in the MiSeq cartridge (i.e. 300 cycles v2) and start the run following Illumina® instructions
7. The resulting fastq is trimmed to eliminate adapters, short reads (<40 nt) and low quality reads and nucleotides. The trimmed fastq is aligned to the specific target reference and to the Hg38 (to calculate human and mitochondrial content) using Bowtie2. The number of mapped reads is calculated by loading the resulting .bam file in the Qualimap program. The % of target reads is calculated by comparing mapped reads to the total.

Protocol for Mitochondria and/or mtNA Enrichment
1. Starting sample could be whole blood (200 µl)
2. Add 20 µl of PLC (0.04 mg/µl)
3. Vortex 10 seconds
4. Incubate 15 min at 37° C. at 1000 rpm
5. Add 200 µl of HL-SAN buffer (5M NaCl, 100 mM MgCl2)
6. Add 10 µl of HL-SAN nuclease (25 U/µl)
7. Vortex 10 seconds
8. Incubate 15 min at 37° C. at 1000 rpm
9. Add 1.4 ml of PBS
10. Centrifuge 10 min at 12,000 g and discard supernatant
11. Add 700 µl pf PBS and resuspend the pellet by pipetting up and down
12. Add additional 700 µl of PBS
13. Centrifuge 10 min at 12,000 g and discard supernatant
14. Add 200 µl pf PBS and resuspend the pellet by pipetting up and down
15. Intact mitochondria are ready to be used
30. To obtain mtDNA and/or mtRNA, extract the NA from the sample with any nucleic acid extraction method. E.g. Extract NA with EasyMAg extraction robot (Biomerieux) standard protocol; select "blood" as matrix and elute in 30 µl of elution buffer Example 1—Identification of Human mtDNA as the Main DNA Present in a Blood Sample after Human NA Depletion Using Phospholipase C (PLC) and Nuclease-Based Depletion Different pathogens (bacteria and fungi) at different concentrations were spiked into human blood. Blood was first treated with phospholipase C (PLC) to selectively lyse human cells and then with a nuclease to eliminate human NA, samples centrifuged, supernatant discarded and the remaining NA (nucleic acids) present in the sample were extracted by different methods, amplified by whole genome amplification and sequenced by whole genome next generation sequencing (NGS) (Miseq, Illumina and Minion, ONT). Bioinformatics analysis was done to assess if we were able to detect the target pathogen and to assess the percentage of the total reads corresponding to that target and also to human DNA.

We discovered that the majority of sequenced reads correspond to human DNA and, specifically, to mitochondrial DNA (mtDNA) (Table 1).

TABLE 1

Percentage sequencing reads of different sources

| | Sample | Pathogen | NGS sequencer | Enrichment method | Extraction method | Pathogen reads (%) | Human reads (%) | mtDNA reads from human total reads (%) |
|---|---|---|---|---|---|---|---|---|
| 1 | 200 ul Blood | E. coli (250 CFU/ml) | Miseq | PLC + nuclease | enzymes mix + Magnapure (Roche) | 0.05 | 99.8 | 88.7 |
| 2 | 200 ul Blood | A. niger (10,000 CFU/ml) | Miseq | PLC + nuclease | enzymes mix + Magnapure (Roche) | 0.84 | 98.8 | 89.0 |
| 3 | 200 ul Blood | E. coli (16,400 CFU/ml) | Miseq | PLC + nuclease | enzymes mix + easyMAg (Biomerieux) | 0.66 | 97.9 | 93.9 |
| | | | MinION | PLC + nuclease | enzymes mix + easyMAg (Biomerieux) | 1.0 (Minimap) 1.5 (WIMP) | 87.9 (Minimap) 77.0 (WIMP) | 98.9 |
| 4 | 200 ul Blood | C. albicans (960 CFU/ml) | Miseq | PLC + nuclease | enzymes mix + easyMAg (Biomerieux) | 0.0004 | 99.2 | 95.9 |
| 5 | 200 ul Blood | A. niger (10,000 CFU/ml) | Miseq | PLC + nuclease | enzymes mix + easyMAg (Biomerieux) | 0.06 | 98.8 | 95.0 |
| 6 | 200 ul Blood | E. coli (49,000 CFU/ml) | Miseq | PLC + nuclease | easyMAg (Biomerieux) | 0.59 | 99.1 | 97.1 |
| 7 | 200 ul Blood | C. albicans (8,350 CFU/ml) | Miseq | PLC + nuclease | enzymes mix + easyMAg (Biomerieux) | 0.01 | 99.3 | 96.8 |
| 8 | 200 ul Blood | C. albicans (8,350 CFU/ml) | Miseq | PLC + nuclease | easyMAg (Biomerieux) | 0.11 | 99.7 | 97.0 |
| 9 | 200 ul Blood | A. niger (10,000 CFU/ml) | Miseq | PLC + nuclease | Bead beating + easyMAg (Biomerieux) | 1.23 | 97.9 | 96.5 |
| | 200 ul Blood | A. niger (10,000 CFU/ml) | MinION | PLC + nuclease | Bead beating + easyMAg (Biomerieux) | 4.4 (Minimap) 3.1 (WIMP) | 85.6 (Minimap) 75.6 (WIMP) | 99.1 |

We performed bioinformatics analysis to see if the whole mtDNA was present in the samples after PLC+DNAse treatment or if only fragments of mtDNA. We found that the whole mitochondrial genome (about 16 kb) was present and well-covered (see FIG. 1). Thus, we hypothesized that PLC did not degrade mitochondria and possibly entire mitochondria were present in the sample. As an alternative hypothesis it could also be possible that the DNAse is more efficient degrading non-circular DNA and since the mtDNA is circular (as is the bacterial DNA) the mtDNA is less sensitive to degradation by DNAse.

Example 2—Identification of Mitochondrial External Membrane Proteins in a Blood Sample after Human NA Depletion Using PLC+Nuclease To check if not only mtDNA but also the whole mitochondria organelle was present in the sample after PLC+ nuclease treatment, Western blot against Mitochondrial import receptor subunit TOM22 homolog (TOM22; UniProt Q9NS69 (UniProt sequence last modified: 23 Jan. 2007), a core component of the mitochondria outer membrane protein translocation pore, was carried out. Whole blood was treated by PLC+DNAse treatment. The supernatant discarded after first centrifugation, the final sample and the original whole blood were analyzed. Briefly, 20 ug of protein of each sample were denatured and loaded in a gel to carry out Western blot using anti-TOM22 antibody.

Figure 2:
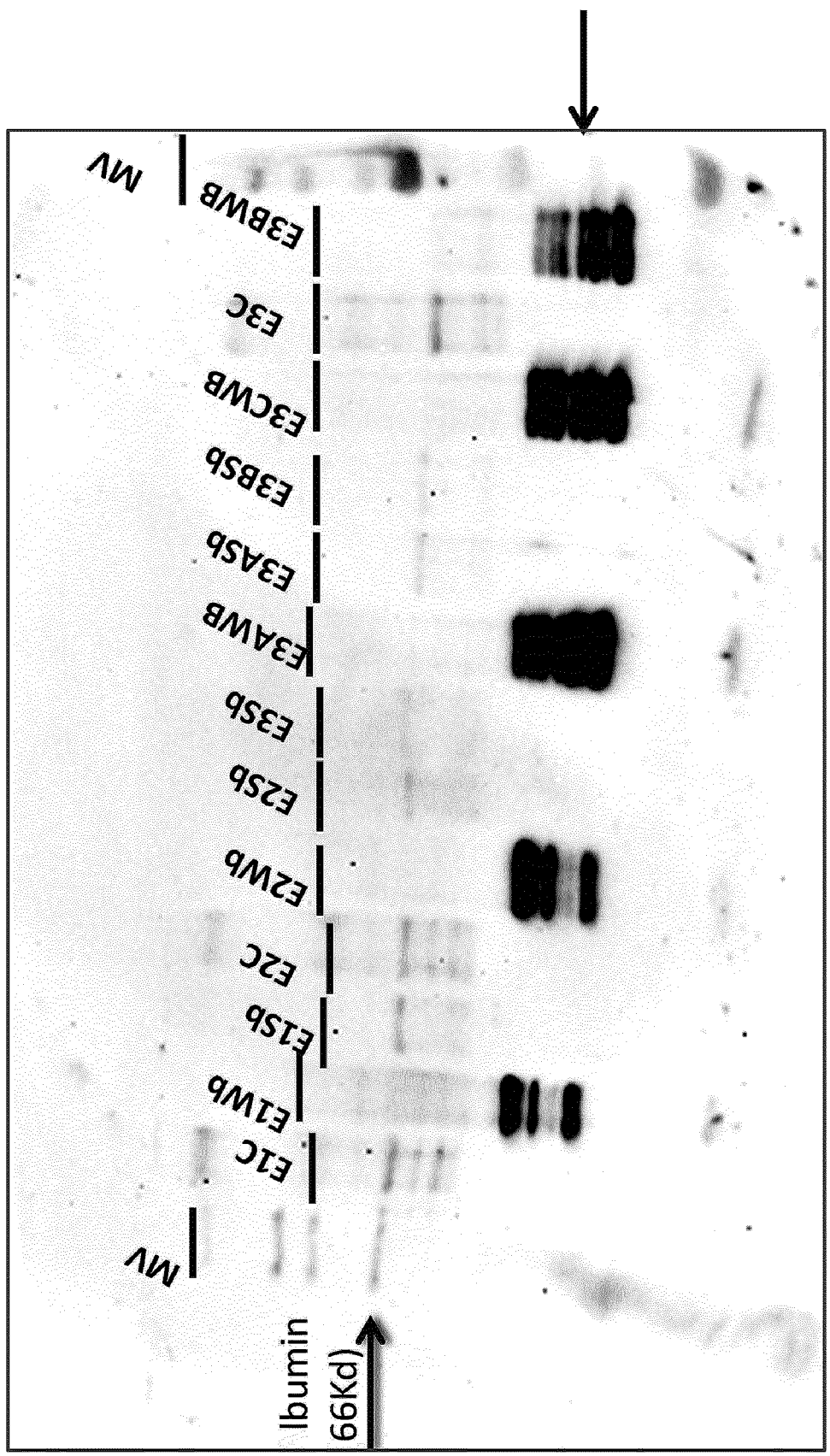
FIG. 2 shows a Western blot for TOM22. Three 3 different blood samples (E1, E2, E3) were checked, E3 was checked in triplicate (E3A, E3B, E3C). C refers to not treated blood, WB to PLC treated samples and Sb to the supernatant from the first centrifugation done to pellet not lysed content. The TOM22 protein weight is around 25 kb, but it makes complexes with other proteins and could be detected at other weights.

The obtained results confirm that TOM22 was present in the sample after human DNA depletion using PLC+nuclease (see FIG. 2), indicating that PLC treatment does not degrade mitochondrial external membrane and, thus, the mtDNA remains in the sample after PLC+nuclease treatment. The whole blood shows no signal due to the low percentage of TOM22 protein compared to the whole protein contain. Albumin is so abundant that gives non-specific signal in the whole blood and supernatant fractions.

Example 3—Confirming Presence of Mitochondria by Cytometry

Figure 3:
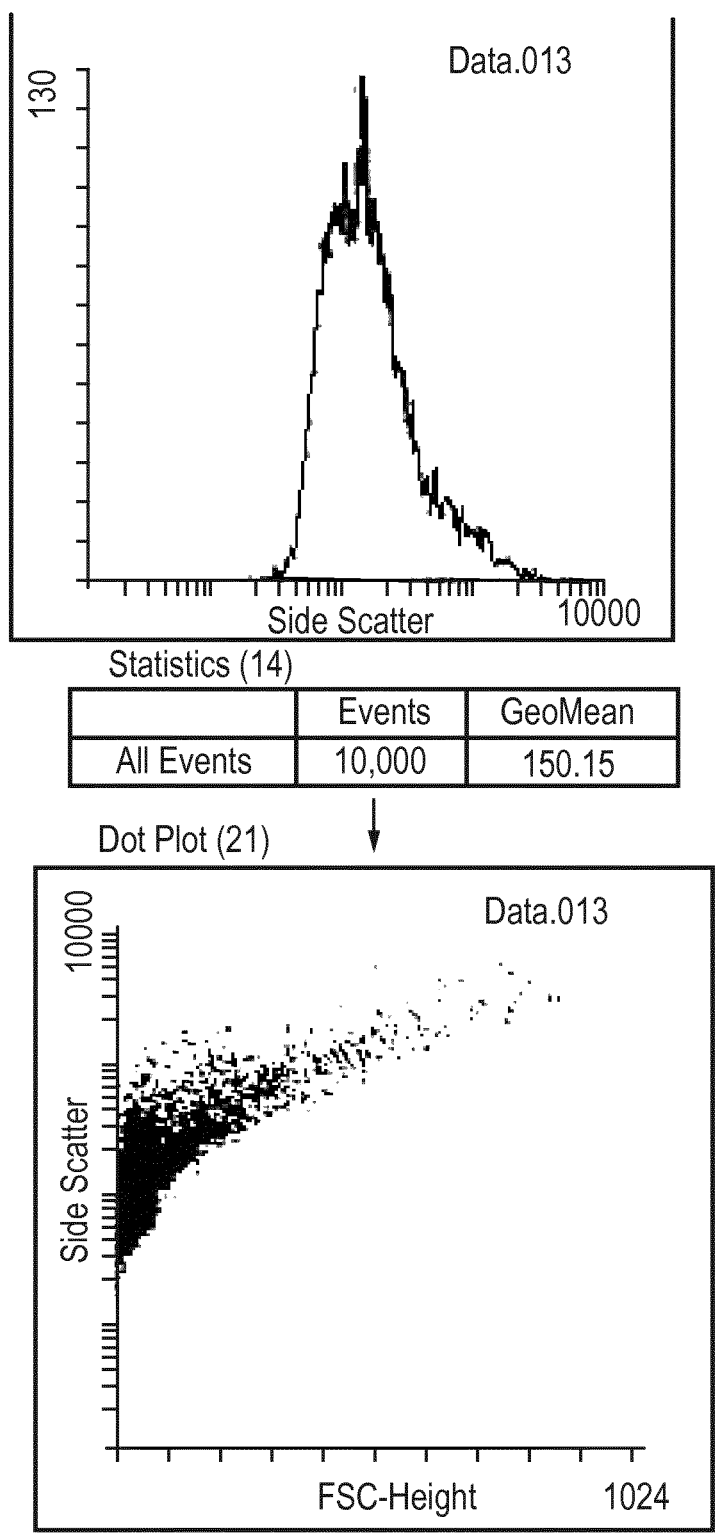
FIG. 3 depicts a FACS output a PLC+nuclease treated sample.

We also confirmed the presence of entire mitochondria by Cytometry. We analyzed a PLC treated sample by Forward as side scattering in a FACSCalibur equipment and saw a unique population with a size/complexity compatible with mitochondria (FIG. 3).

Example 4—Depletion of Human mtNA Using a Mitochondrial Isolation Method Based on Anti-Mitochondrial Antibodies We eliminated the human mtNA that remained in the sample after treatment of blood with PLC and nuclease by eliminating the mitochondria organelles.

Figure 4:
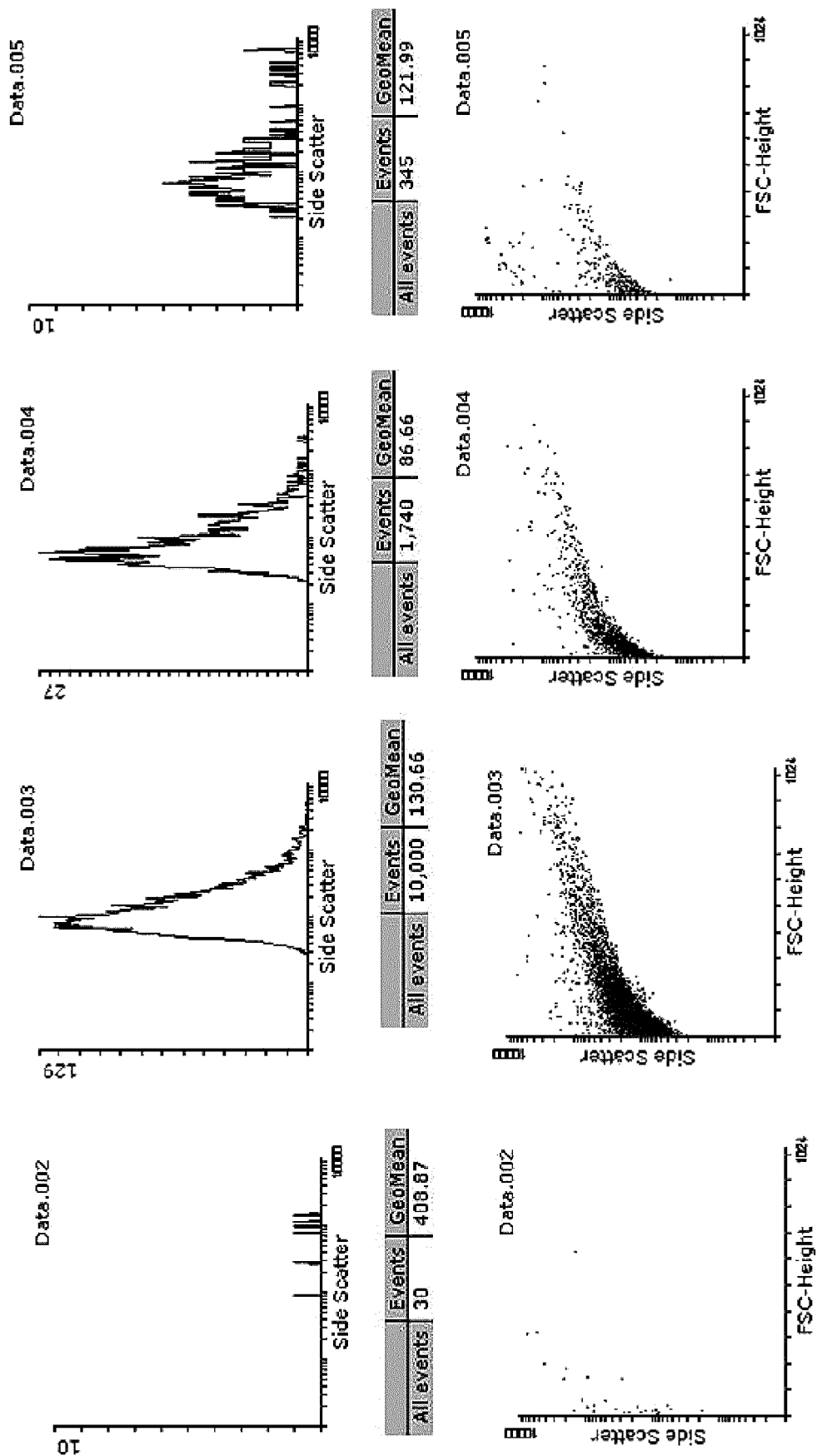
FIG. 4 shows cytometer plots. Sample codes correspond to samples indicated in Table 2 (excepting 005, 006, 009 and 010 that correspond to washes of the column between the elution of the sample and the recovery of retained mitochondria).
Figure 4:
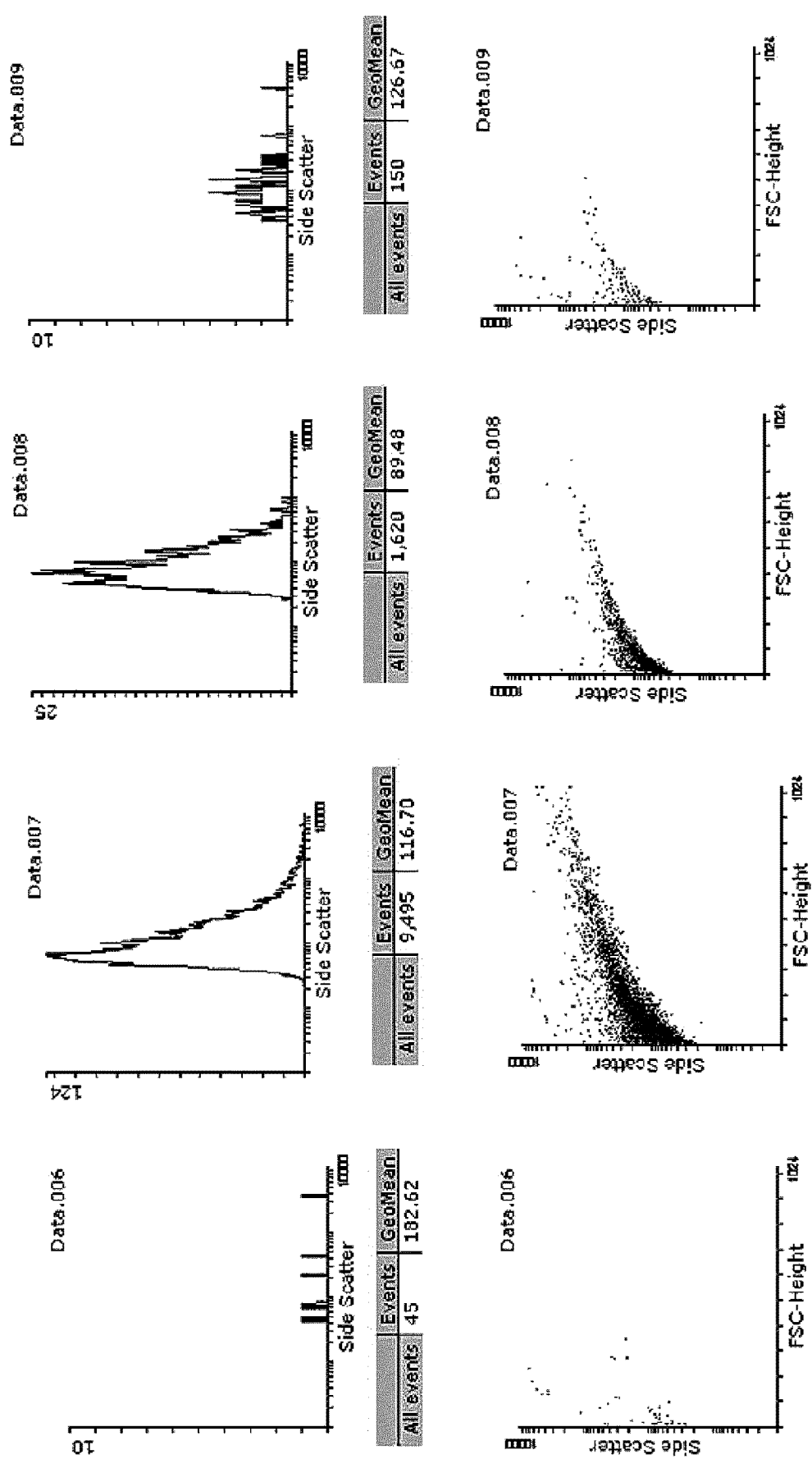
Figure 4:
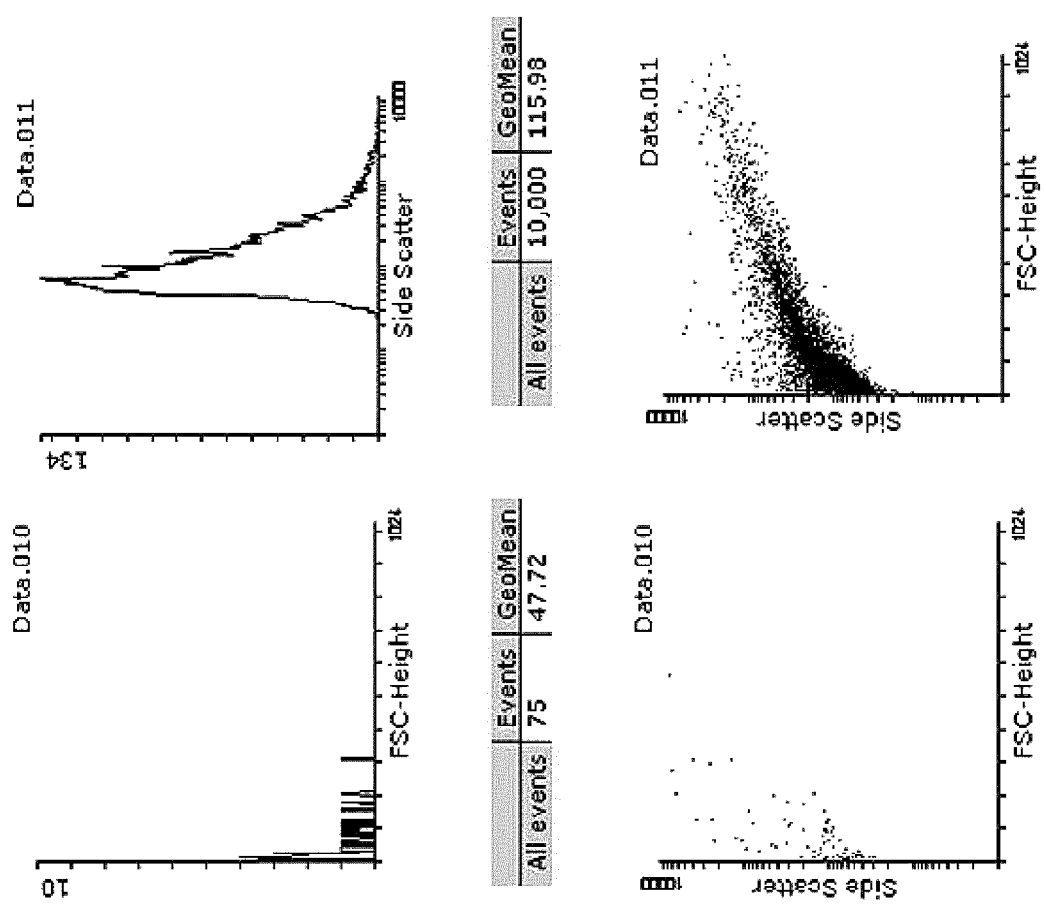

We used a commercial mitochondria isolation method based on antibodies (Miltenyi Biotech kit). Specifically, after PLC and nucleasese treatment, mitochondria were magnetically labeled with Anti-TOM22 nanobeads, human, which bind to TOM22. The sample was loaded onto a column and placed in a magnetic separator. After washing, magnetically labeled mitochondria were retained on the column and the rest of the sample was eluted. To check the presence of mitochondria after the depletion step, we processed the sample with the flow cytometer FACSCalibur. Elution buffer and anti-TOM22 beads were used as negative controls and a sample treated with PLC+nuclease without mitochondrial depletion as positive control. As shown in Table 2 and FIG. 4, the majority of mitochondria were retained in the column and only a small fraction remained in the eluted sample, which was then the sample utilized (see further below).

TABLE 2

Column retention of mitochondria

| Treatment | Sample | Events | Counting time | Code in the Cytometer plot figure |
|---|---|---|---|---|
| NA | Elution buffer (Control) | 45 | 1 min 15 s | — |
| NA | Anti-TOM22 beads (Control) | 30 | 1 min | 002 |
| PLC + nucleasese | PLC + nuclease treated sample | 10000 | 45 s | 003 |
| PLC + nucleasese + mitochondria 1 isolation (anti-TOM22) sample 1 | Eluate | 1740 | 45 s | 004 |
| | Column retained fraction | 8850 | 45 s | 007 |
| PLC + nucleasese + mitochondria 1 isolation (anti-TOM22) sample 2 | Eluate | 1620 | 45 s | 008 |
| | Column retained fraction | 10000 | 36 s | 011 |

Depletion of human mtDNA after mitochondria removal was evaluated also by qPCR, after extracting the NA from the samples. It was observed that mtDNA decreased between 6.5-9.1 times in samples treated with PLC+nuclease+mitochondrial removal compared to samples in which only PLC+nuclease treatment was performed (Table 3).

TABLE 3

Depletion of human mtDNA assessed by qPCR

| Microorganism | Treatment | Target | Ct | Human mtDNA decrease times compared to PLC + nuclease |
|---|---|---|---|---|
| E. coli (53,733 CFU/ml) | PLC + Nuclease | mtDNA | 18.4 | — |
| | PLC + Nuclease + mitochondria depletion | mtDNA | 21.1 | 6.5 |
| E. coli (11,573 CFU/ml) | PLC + Nuclease | mtDNA | 18.6 | — |
| | PLC + Nuclease + mitochondria depletion | mtDNA | 21.6 | 8.0 |
| C. albicans (49,443 CFU/ml) | PLC + Nuclease | mtDNA | 18.5 | — |
| | PLC + Nuclease + mitochondria depletion | mtDNA | 21.6 | 8.6 |
| C. albicans (10,649 CFU/ml) | PLC + Nuclease | mtDNA | 18.5 | — |
| | PLC + Nuclease + mitochondria depletion | mtDNA | 21.7 | 9.1 |

It was checked by qPCR whether microorganisms remain in the eluate or were eliminated when mitochondria were depleted with the antibody-based method. Sample treated only with PLC+nucleasese was used as control. It was found that E. coli was not affected by the method, remaining in the eluate (Table 4). A decrease in C. albicans was detected. Since Candida albicans appears at high Cts, we have carried out whole genome amplification and then qPCR to better detect the pathogen and the eluted Candida was comparable to the original so it was not retained by the column (data not shown).

TABLE 4

Pathogen DNA as assessed by qPCR following indicated treatments

| Micro-organism | Treatment | Target | Ct | Pathogen DNA decrease times compared to PLC + nuclease |
|---|---|---|---|---|
| E. coli (53,733 CFU/ml) | PLC + Nuclease | E. coli | 26.8 | — |
| | PLC + Nuclease + mitochondria depletion | E. coli | 26.6 | 1.1 |
| E. coli (11,573 CFU/ml) | PLC + Nuclease | E. coli | 29.3 | — |
| | PLC + Nuclease + mitochondria depletion | E. coli | 29.3 | 0.0 |
| C. albicans (49,443 CFU/ml) | PLC + Nuclease | C. albicans | 35.0 | — |
| | PLC + Nuclease + mitochondria depletion | C. albicans | 35.5* | 1.4 |
| C. albicans (10,649 CFU/ml) | PLC + Nuclease | C. albicans | 35.2* | — |
| | PLC + Nuclease + mitochondria depletion | C. albicans | 36.8* | 3.0 |

*High Ct outside reliable quantitative range of the PCR, indicating potentially unreliable results.

Example 5—Depletion of Human mtNA Using a Mitochondrial Isolation Method Based in Lysis of Mitochondria with Saponin In an attempt to improve upon the PLC+nuclease method for depletion of host NA, the present inventors opted to add a second lysis step utilizing saponin to lyse the mitochondria not lysed by PLC. This method was then compared to the anti-TOM22 column based method described in Example 4 above.

Aliquots of 200 μl whole blood were treated with PLC+nuclease followed by PBS washes (centrifugation plus supernatant discard), pellet resuspended in 200 μl of PBS, pooled and redistributed in aliquots of 100 μl. Each suspension of 100 μl was treated with, respectively:

1. Saponin 5%: addition of 200 μl of Saponin 5% followed by nuclease treatment and PBS washes.
2. Saponin 1%: addition of 200 μl of Saponin 1% followed by nuclease treatment and PBS washes.
3. Column Milteny: Incubation of the sample with beads covered by anti-TOM22 antibodies, column loading and eluate recovered (sample 3A). Also recovered the retained mitochondria after column washes (sample 3B).

Nucleic acids from all the samples were extracted and checked by qPCR with a Taqman® probe specific for mtDNA. The results are shown in Table 5.

TABLE 5 qPCR assessment of mtDNA after indicated treatments

| Sample | Target | Ct | Ct reference | Decrease times compared to control | Treatment (s) |
|---|---|---|---|---|---|
| Control (PLC)-1 | Mitoc | 15.76 | 15.84 | — | Blood + PLC |
| Control (PLC)-2 | Mitoc | 15.92 | | — | Blood + PLC |
| Sample 1 | Mitoc | 22.60 | | 108.44 | Blood + PLC + 2° Saponin (5%) |
| Sample 2 | Mitoc | 22.68 | | 114.64 | Blood + PLC + 2° Saponin (1%) |
| Sample 3A | Mitoc | 20.37 | | 23.11 | Blood + PLC + Column MS MACS |
| Sample 3B | Mitoc | 18.92 | | 8.46 | Blood + PLC + Column MS MACS – Mitoc |

Example 6—Pathogen DNA Relative Enrichment by Using PLC+Nuclease Followed by Saponin+Nuclease Since the second lysis step based on saponin was found to provide significant depletion of mtDNA, it was decided to test with samples spiked with bacteria and fungi.

Ten aliquots of 200 μl whole blood were spiked with bacteria (E. coli and S. aureus) and fungi (Candida) and were then treated with PLC+nuclease followed by PBS washes (centrifugation plus supernatant discard), resuspended in 200 μl PBS and divided in 2 aliquots of 100 μl. One aliquot was designated as control and the other was treated with 200 μl of 1% saponin+nuclease+PBS washes.

All the samples (10 PLC+10 PLC+saponin) were analyzed by qPCR for human and mitochondrial DNA. The samples treated with PLC are shown with a B suffix (e.g. "Sample 1B"); those treated with PLC+saponin are shown with a C suffix (e.g. "Sample 1C").

The results obtained demonstrate significant reduction of mitochondrial DNA content (approximately 50-fold reduction) and a more efficient genomic DNA (gDNA) (i.e. nuclear DNA) depletion (see Tables 6 and 7). The qPCR for each of the microorganisms shows no significant reduction of microbial DNA content (see Tables 8, 9 and 10).

From the 10 samples, we selected 5 of them treated with PLC+saponin, including 2 samples of each bacteria and one Candida and carried out next generation sequencing (NGS) analysis by Minion and also by MiSeq. The results are shown in Table 11. The percentage of sequence reads from human DNA (nuclear and mitochondria) was very significantly depleted by the PLC+nuclease+Saponin+nuclease treatment, which led to a very significant relative enrichment of the pathogen sequence reads (over 90% in the case of S. aureus sample 4 by Minion WIMP sequencing—see Table 11).

Figure 5:
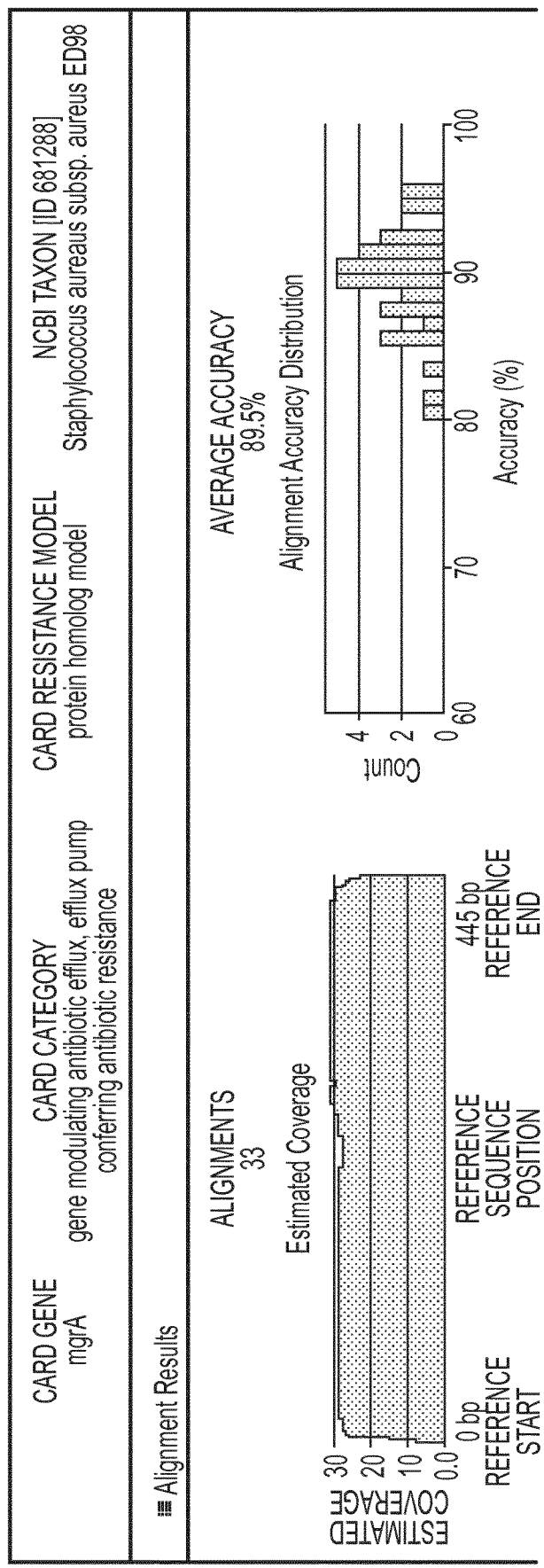
FIG. 5 shows an example of gene resistance detection by NGS. A blood sample spiked with *S. aureus* was treated with PLC+nuclease+Saponin+nuclease, extracted and prepared for being sequenced in the MinION sequencer. The raw data analysis was carried out with the ARMA software (Oxford Nanopore Technologies, ONT) and the figure shows one of the resistance genes detected.

The obtained data indicates that the method is also suitable for antibiotic resistance detection by known molecular mechanism (for example, the presence of genes and/or mutations conferring resistance to specific antibiotics). A representative example is shown in FIG. 5.

TABLE 6

| | | | | | | Decrease times compared to WHOLE BLOOD control |
|---|---|---|---|---|---|---|
| Sample | Microorganism | Treatment | Target | Ct | Ct reference | |
| Sample 1 | — | Control | Human | 25.50 | 25.25 | |
| Sample 3 | E. coli (13,733 cfu/ml) | Control | Human | 25.01 | | |
| Sample 1B | — | PLC | Human | 36.98 | | 3376 |
| Sample 1C | — | PLC + Saponin | Human | Undetermined | | Not detectable |
| Sample 3B | E. coli (13,733 cfu/ml) | PLC | Human | 36.53 | | 248 |
| Sample 3C | E. coli (13,733 cfu/ml) | PLC + Saponin | Human | Undetermined | | Not detectable |
| Sample 4B | E. coli (1,373 cfu/ml) | PLC | Human | 36.09 | | 1830 |
| Sample 4C | E. coli (1,373 cfu/ml) | PLC + Saponin | Human | Undetermined | | Not detectable |
| Sample 5B | C. albicans (12,000 cfu/ml) | PLC | Human | Undetermined | | Not detectable |
| Sample 5C | C. albicans (12,000 cfu/ml) | PLC + Saponin | Human | Undetermined | | Not detectable |
| Sample 6B | C. albicans (1,200 cfu/ml) | PLC | Human | 37.07 | | 3601 |
| Sample 6C | C. albicans (1,200 cfu/ml) | PLC + Saponin | Human | Undetermined | | Not detectable |
| Sample 7B | C. albicans (120 cfu/ml) | PLC | Human | 38.35 | | 8770 |
| Sample 7C | C. albicans (120 cfu/ml) | PLC + Saponin | Human | Undetermined | | Not detectable |
| Sample 8B | S. aureus (586,833 cfu/ml) | PLC | Human | 36.22 | | 2001 |
| Sample 8C | S. aureus (586,833 cfu/ml) | PLC + Saponin | Human | Undetermined | | Not detectable |
| Sample 9B | S. aureus (58,683 cfu/ml) | PLC | Human | 36.83 | | 3054 |
| Sample 9C | S. aureus (58,683 cfu/ml) | PLC + Saponin | Human | Undetermined | | Not detectable |
| Sample 10B | S. aureus (5,868 cfu/ml) | PLC | Human | 36.88 | | 3156 |
| Sample 10C | S. aureus (5,868 cfu/ml) | PLC + Saponin | Human | 38.44 | | 9316 |
| CN | | Water | Human | Undetermined | | Not detectable |

TABLE 7

Data for mtDNA content analysis

| Sample | Micro-organism | Treatment | Target | Ct | Ct reference | Decrease times compared to corresponding PLC control |
|---|---|---|---|---|---|---|
| Sample 1 | — | Control | Mitoc | 19.84 | 19.83 | |
| Sample 3 | E. coli (13,733 cfu/ml) | Control | Mitoc | 19.81 | | |
| Sample 1B | — | PLC | Mitoc | 17.71 | | |
| Sample 1C | — | PLC + Saponin | Mitoc | 23.37 | | 50.5 |
| Sample 3B | E. coli (13,733 cfu/ml) | PLC | Mitoc | 17.44 | | |
| Sample 3C | E. coli (13,733 cfu/ml) | PLC + Saponin | Mitoc | 23.16 | | 43.7 |
| Sample 4B | E. coli (1,373 cfu/ml) | PLC | Mitoc | 17.57 | | |
| Sample 4C | E. coli (1,373 cfu/ml) | PLC + Saponin | Mitoc | 23.07 | | 41.0 |
| Sample 5B | C. albicans (12,000 cfu/ml) | PLC | Mitoc | 17.74 | | |
| Sample 5C | C. albicans (12,000 cfu/ml) | PLC + Saponin | Mitoc | 23.09 | | 41.6 |
| Sample 6B | C. albicans (1,200 cfu/ml) | PLC | Mitoc | 17.30 | | |
| Sample 6C | C. albicans (1,200 cfu/ml) | PLC + Saponin | Mitoc | 23.12 | | 42.2 |
| Sample 7B | C. albicans (120 cfu/ml) | PLC | Mitoc | 17.52 | | |
| Sample 7C | C. albicans (120 cfu/ml) | PLC + Saponin | Mitoc | 24.80 | | 135.5 |
| Sample 8B | S. aureus (586,833 cfu/ml) | PLC | Mitoc | 17.53 | | |
| Sample 8C | S. aureus (586,833 cfu/ml) | PLC + Saponin | Mitoc | 23.23 | | 45.7 |
| Sample 9B | S. aureus (58,683 cfu/ml) | PLC | Mitoc | 17.18 | | |
| Sample 9C | S. aureus (58,683 cfu/ml) | PLC + Saponin | Mitoc | 23.07 | | 40.9 |
| Sample 10B | S. aureus (5,868 cfu/ml) | PLC | Mitoc | 16.97 | | |
| Sample 10C | S. aureus (5,868 cfu/ml) | PLC + Saponin | Mitoc | 23.04 | | 40.2 |
| CN | Water | | Mitoc | Un-determined | | Not detectable |

TABLE 8

Data for microorganism E. coli

| Sample | Microorganism | Treatment | Target | Ct |
|---|---|---|---|---|
| Sample 3 | E. coli (13,733 cfu/ml) | Control | E coli | 32.98 |
| Sample 3B | E. coli (13,733 cfu/ml) | PLC | E coli | 30.93 |
| Sample 3C | E. coli (13,733 cfu/ml) | PLC + Saponin | E coli | 31.96 |
| Sample 4 | E. coli (1,373 cfu/ml) | Control | E coli | 37.44 |
| Sample 4B | E. coli (1,373 cfu/ml) | PLC | E coli | 34.41 |
| Sample 4C | E. coli (1,373 cfu/ml) | PLC + Saponin | E coli | 35.82 |
| Sample E coli 105 | E. coli (13,733 cfu/ml) | Original culture | E coli | 31.20 |
| Water | | | E coli | Undetermined |

TABLE 9

Data for microorganism C. albicans

| Sample | Microorganism | Treatment | Target | Ct |
|---|---|---|---|---|
| Sample 5 | C. albicans (12,000 cfu/ml) | Control | C albicans | 33.37 |
| Sample 5B | C. albicans (12,000 cfu/ml) | PLC | C albicans | 35.97 |
| Sample 5C | C. albicans (12,000 cfu/ml) | PLC + Saponin | C albicans | 35.02 |
| Sample 6 | C. albicans (1,200 cfu/ml) | Control | C albicans | Undetermined |
| Sample 6B | C. albicans (1,200 cfu/ml) | PLC | C albicans | Undetermined |
| Sample 6C | C. albicans (1,200 cfu/ml) | PLC + Saponin | C albicans | 36.58 |
| Sample 7 | C. albicans (120 cfu/ml) | Control | C albicans | Undetermined |
| Sample 7B | C. albicans (120 cfu/ml) | PLC | C albicans | Undetermined |
| Sample 7C | C. albicans (120 cfu/ml) | PLC + Saponin | C albicans | Undetermined |
| Sample Calbicans105 | C. albicans (1,200 cfu/ml) | Original culture | C albicans | 36.66 |
| Water | | | C albicans | Undetermined |

TABLE 10

Data for microorganism S. aureus

| Sample | Microorganism | Treatment | Target | Ct |
|---|---|---|---|---|
| Sample 8 | S. aureus (586,833 cfu/ml) | Control | S. aureus | 34.33 |
| Sample 8B | S. aureus (586,833 cfu/ml) | PLC | S. aureus | 33.85 |
| Sample 8C | S. aureus (586,833 cfu/ml) | PLC + Saponin | S. aureus | 30.27 |
| Sample 9 | S. aureus (58,683 cfu/ml) | Control | S. aureus | 38.69 |
| Sample 9B | S. aureus (58,683 cfu/ml) | PLC | S. aureus | 34.79 |
| Sample 9C | S. aureus (58,683 cfu/ml) | PLC + Saponin | S. aureus | 34.32 |
| Sample 10 | S. aureus (5,868 cfu/ml) | Control | S. aureus | Undetermined* |
| Sample 10B | S. aureus (5,868 cfu/ml) | PLC | S. aureus | 38.58 |
| Sample 10C | S. aureus (5,868 cfu/ml) | PLC + Saponin | S. aureus | Undetermined* |
| CN | Water | | S. aureus | Undetermined |

*The spiked quantity is in the detection limit

TABLE 11

Data from NGS analysis

| | Sample | Pathogen | Enrichment method | Extraction method | NGS sequencer | Target Pathogen reads (%) | Human reads (%) | mtDNA reads from human total reads (%) |
|---|---|---|---|---|---|---|---|---|
| 1 | 200 ul Blood | E. coli (13,733 cfu/ml) | PLC + Nuclease + Saponin + Nuclease | easyMAg (Biomerieux) | Miseq Minion WIMP | 86.59% 84.0% | 0.30% 0.1% | 56% ND |
| 2 | 200 ul Blood | E. coli (1,373 cfu/ml) | PLC + Nuclease + Saponin + Nuclease | easyMAg (Biomerieux) | Miseq Minion WIMP | 53.85% 47.4% | 0.90% 0.5% | 76% ND |
| 3 | 200 ul Blood | C. albicans (1,200 cfu/ml) | PLC + Nuclease + Saponin + Nuclease | easyMAg (Biomerieux) | Miseq Minion WIMP | 23.3% 28.8% | 3.8% 2.0% | 9% ND |

TABLE 11-continued

Data from NGS analysis

| Sample | Pathogen | Enrichment method | Extraction method | NGS sequencer | Target Pathogen reads (%) | Human reads (%) | mtDNA reads from human total reads (%) |
|---|---|---|---|---|---|---|---|
| 4 | 200 ul Blood | S. aureus (58,683 cfu/ml) | PLC + Nuclease + Saponin + Nuclease | easyMAg (Biomerieux) | Miseq Minion WIMP | 87.5% 94.1% | 0.40% 0.1% | 37% ND |
| 5 | 200 ul Blood | S. aureus (5,868 cfu/ml) | PLC + Nuclease + Saponin + Nuclease | easyMAg (Biomerieux) | Miseq Minion WIMP | 20.6% 38.3% | 7.30% 6.2% | 5% ND |

Example 7—Comparison of Human Nucleic Acid Depletion by Using PLC+Nuclease Followed by Saponin+Nuclease Vs. Only PLC+Nuclease Method and Vs. Only Saponin+Nuclease We next carried out an experiment with 2 samples (*E. coli* and *S. aureus*) treated in parallel with:
1. PLC+nuclease;
2. Saponin+Nuclease
3. PLC+Nuclease+Saponin+Nuclease (in accordance with the method of the invention).

One ml of whole blood was spiked with *E. coli* and other 1 ml of whole blood was spiked with *S. aureus* and aliquots of 200 µl were made. Each aliquot was treated in accordance with one of the above two methods, as was a non-spiked whole blood control.

We carried out qPCR to detect human gDNA and mtDNA. The major human and mitochondrial decrease was observed for the PLC+Saponin method (data not shown).

The extracted DNA was amplified and a library was prepared with Nextera XT and, a run of MiSeq including *E. coli* and *S. aureus* treated with the 3 different methods was performed. The results are shown in Table 12. The results demonstrate that method 3 above (PLC+Nuclease+Saponin+Nuclease) achieved the greatest relative enrichment of Pathogen sequence reads for both of the pathogen species tested.

TABLE 12

NGS data for human DNA and pathogen DNA for the identified enrichment methods

| Sample | Pathogen | Enrichment method | Extraction method | NGS sequencer | Pathogen reads (%) | Human reads (%) | mtDNA reads from human total reads (%) |
|---|---|---|---|---|---|---|---|
| 200 ul Blood | E. coli (25,383 cfu/ml) | PLC + Nuclease | easyMAg (Biomerieux) | Miseq | 6.85 | 92.07 | 86.17 |
| 200 ul Blood | E. coli (25,383 cfu/ml) | Saponin + Nuclease | easyMAg (Biomerieux) | Miseq | 6.78 | 92.26 | 49.32 |
| 200 ul Blood | E. coli (25,383 cfu/ml) | PLC + Nuclease + Saponin + Nuclease | easyMAg (Biomerieux) | Miseq | 87.75 | 0.97 | 56.14 |
| 200 ul Blood | S. aureus (11,083 cfu/ml) | PLC + Nuclease | easyMAg (Biomerieux) | Miseq | 0.73 | 98.83 | 88.74 |
| 200 ul Blood | S. aureus (11,083 cfu/ml) | Saponin + Nuclease | easyMAg (Biomerieux) | Miseq | 0.11 | 99.45 | 92.23 |
| 200 ul Blood | S. aureus (11,083 cfu/ml) | PLC + Nuclease + Saponin + Nuclease | easyMAg (Biomerieux) | Miseq | 50.69 | 21.81 | 38.34 |

Example 8—Minimal Spontaneous Lysis of Cells During Isolation and Storage of Human Whole Blood Samples Spontaneous lysis of red cells (autohemolysis) is believed to be low in the absence of specific treatment to lyse cells. For example, Young et al., *Blood* (1956), Vol. 11, pp. 977-997, report a rate of autohemolysis in red cells below 0.5% when the sample was stored for 48 hrs without further manipulation.

The present inventors analyzed the spontaneous lysis during an 7-day period for 3 whole blood samples. Identical aliquots of the whole samples were stored at room temperature (RT) and at 4° C. At concrete times (Day 0 to Day 7) plasma samples were prepared following two different centrifugation speeds: standard for plasma preparation, 900×g, obtaining an acellular fraction containing released mitochondria (since they do not precipitate at this speed) and higher, 10,000×g were the majority of mitochondria are precipitated and, therefore, the content of this fraction is acellular and with no mitochondria. The level of hemolysis of red cells (despite not having DNA, their rupture is considered the indicator of lysis since the erythrocytes are the most fragile blood cell type), the gDNA content and also the mtDNA content in the plasma were measured to determine whether both data change during the time, showing the lysis of the cells and mitochondria during the storage.

The setup of the experiment was as follows:

|  |  | Storage Time | | | | | | | |
| --- | --- | --- | --- | --- | --- | --- | --- | --- | --- |
|  |  | 0 h | 24 h | 48 h | 72 h | 96 h | 120 h | 144 h | 168 h |
| 4° C. | Whole blood | X | | | | | | | |
|  | Plasma 900 × g | | X | X | X | X | | | X |
|  | Plasma 10000 × g | | X | X | X | X | | | X |
| RT | Plasma 900 × g | | X | X | X | X | | | X |

3 different whole blood samples
250 µl aliquots for each condition (stored at RT or 4° C. during 7 days).
X: sampling 80 µl:
20 µl to analyze hemolysis by measuring 412 nm Absorbance after diluting 1:50 in water (1:5000 in case of whole blood because it is too much concentrated and the Absorbance is saturated using 1:50)
and 60 µl frozen for further DNA extraction. 50 µl were extracted using easyMAG (Biomereux) and eluted in 25 µl. Four µl were used to check gDNA by qPCR using an specific taqman assay for gDNA, and other 4 µl were used to analysed mtDNA content also by qPCR with a specific Taqman assay
The % of lysis has been obtained comparing the initial measure of each parameter within equivalent fractions at time 0. It has been also calculated the plasma fraction content for each parameter with total whole blood measures.

Results

Measures correspond to whole blood of 2 tubes collected from 3 different individuals: 6 samples for each measure point.

The table below shows % of lysis based on the measures for the 3 studied parameters compared to whole blood measures (first column: % vs Total) and to each corresponding fraction at point 0 (Second column: % increase vs same fraction time 0; i.e. % of measure for plasma at time 72 h RT of the one of plasma at time 0). The % of lysis due to storage is the corresponding to the second column, since the first is only included to show that there is already some content of hemoglobin, mtDNA and gDNA in the plasma fraction with no treatment of time of storage.

As shown in the table, typical sample preparation and storage (e.g. 4° C. for up to 48 hours), results in essentially no lysis (all measured parameters approximately zero). Even after 96 and 168 hours at standard storage (4° C.), lysis remains low at around 2% and 4%, respectively, looking to gDNA, even lower looking at hemolysis and about 7.5% looking at mtDNA (less confidence due to its high desvest). Even in the case of having the blood at RT during 48 h the lysis is almost 0. No long storage at RT is carried out in the routine of whole blood handling.

The present inventors therefore conclude that spontaneous lysis, i.e. in the absence of a treatment to cause lysis, is low under typical conditions.

| Time | Temp | Centrif xg | HEMOLYSIS MEASURE | | | | mtDNA MEASURE | | | |
| --- | --- | --- | --- | --- | --- | --- | --- | --- | --- | --- |
|  |  |  | % vs Total Average | % increase vs same fraction t0 Average | % vs Total Devest | % increase vs same fraction t1 Devest | % vs Total Average | % increase vs same fraction t2 Average | % vs Total Devest | % increase vs same fraction t3 Devest |
| 0 | — | 900 | 0.32% |  | 0.05% |  | 4.5% |  | 4.4% | 0.0% |
| 24 h | 4° C. | 900 | 0.35% | 0.03% | 0.10% | 0.11% |  |  |  |  |
| 48 h | 4° C. | 900 | 0.43% | 0.11% | 0.16% | 0.18% | 4.2% | −0.4% | 2.2% | 5.6% |
| 72 h | 4° C. | 900 | 0.39% | 0.07% | 0.09% | 0.08% |  |  |  |  |
| 96 h | 4° C. | 900 | 0.56% | 0.24% | 0.07% | 0.09% | 12.3% | 7.8% | 15.7% | 13.5% |
| 168 h | 4° C. | 900 | 0.55% | 0.23% | 0.10% | 0.08% | 12.1% | 7.5% | 11.6% | 13.7% |
| 24 h | RT | 900 | 0.28% | −0.04% | 0.12% | 0.14% |  |  |  |  |
| 48 h | RT | 900 | 0.23% | −0.09% | 0.04% | 0.07% | 4.8% | 0.3% | 2.8% | 4.7% |
| 72 h | RT | 900 | 0.32% | 0.00% | 0.12% | 0.13% |  |  |  |  |
| 96 h | RT | 900 | 0.45% | 0.14% | 0.14% | 0.14% | 12.7% | 8.2% | 6.8% | 3.3% |
| 168 h | RT | 900 | 0.84% | 0.52% | 0.24% | 0.28% | 7.1% | 2.5% | 4.5% | 3.7% |
| 0 | — | 10000 | 0.31% |  | 0.06% |  | 0.1% | 0.0% | 0.1% | 0.0% |
| 24 h | 4° C. | 10000 |  |  |  |  |  |  |  |  |
| 48 h | 4° C. | 10000 | 0.36% | 0.05% | 0.05% | 0.09% | 1.9% | 1.8% | 3.5% | 3.5% |
| 72 h | 4° C. | 10000 | 0.64% | 0.33% | 0.16% | 0.18% |  |  |  |  |

-continued

| | | | | | | | | | | |
|---|---|---|---|---|---|---|---|---|---|---|
| 96 h | 4° C. | 10000 | 0.44% | 0.13% | 0.09% | 0.07% | 1.3% | 1.2% | 0.9% | 0.9% |
| 168 h | 4° C. | 10000 | 0.43% | 0.12% | 0.06% | 0.08% | 2.7% | 2.6% | 2.7% | 2.7% |

| | gDNA MEASURE | | | |
|---|---|---|---|---|
| Time | % vs Total Average | % increase vs same fraction t4 Average | % vs Total Devest | % increase vs same fraction t5 Devest |
| 0 | 0.7% | 0.0% | 0.8% | 0.0% |
| 24 h | | | | |
| 48 h | 0.3% | −0.4% | 0.2% | 0.8% |
| 72 h | | | | |
| 96 h | 2.8% | 2.1% | 5.5% | 4.8% |
| 168 h | 4.6% | 3.9% | 3.0% | 2.9% |
| 24 h | | | | |
| 48 h | 1.6% | 0.9% | 1.2% | 1.4% |
| 72 h | | | | |
| 96 h | 6.4% | 5.7% | 4.0% | 3.3% |
| 168 h | 28.5% | 27.9% | 18.7% | 17.9% |
| 0 | 0.1% | 0.0% | 0.1% | 0.0% |
| 24 h | | | | |
| 48 h | 0.4% | 0.3% | 0.5% | 0.4% |
| 72 h | | | | |
| 96 h | 0.4% | 0.3% | 0.2% | 0.1% |
| 168 h | 0.8% | 0.7% | 0.5% | 0.5% |

All references cited herein are incorporated herein by reference in their entirety and for all purposes to the same extent as if each individual publication or patent or patent application was specifically and individually indicated to be incorporated by reference in its entirety.

The specific embodiments described herein are offered by way of example, not by way of limitation. Any sub-titles herein are included for convenience only, and are not to be construed as limiting the disclosure in any way.

The invention claimed is:

1. A method for depleting host nucleic acid in a biological sample, said sample having been previously obtained from an animal host and having been subjected to treatment to lyse host cells present within the sample, said treatment to lyse host cells being a treatment with a cytolysin, and wherein said sample has been subjected to a treatment to deplete nucleic acid released from host cells within said sample or otherwise to render such nucleic acid unidentifiable, the method comprising:
(a) depleting host mitochondria or host mitochondrial deoxyribonucleic acid (mtDNA) present in the treated sample; and
(b) extracting and/or analysing remaining nucleic acid from the treated sample;
wherein step (a) comprises:
(i) adding a detergent to said treated sample;
(ii) at least partial removal of host mitochondria by contacting the treated sample with an immobilised binding agent that selectively binds mitochondria; or
(iii) extraction of whole nucleic acids and further capture of mitochondrial DNA using a panel of DNA and/or RNA and/or PNA baits that target the host mitochondrial genome; and
wherein step (a) further comprises adding a nuclease to said treated sample.

2. The method according to claim 1, wherein said detergent comprises: saponin, digitonin, and/or filipin.

3. The method according to claim 1, wherein the binding agent comprises an antibody that selectively binds a protein present in the outer membrane of the mitochondria.

4. The method according to claim 3, wherein the antibody selectively binds Mitochondrial import receptor subunit TOM22 homolog (TOM22).

5. The method according to claim 1, wherein step (a) comprises extraction of whole nucleic acids and further RNA-guided DNA endonuclease enzyme-mediated recognition of host mitochondrial DNA using a sgRNA that targets said DNA endonuclease enzyme to a host mitochondrial DNA target sequence.

6. The method according to claim 1, wherein the treatment to which the sample has been subjected to lyse host cells is a treatment that is effective to lyse at least 3% of the host cells in the sample.

7. The method according to claim 1, wherein the cytolysin comprises a phospholipase C.

8. A method for depleting host nucleic acid in a biological sample, said sample having been previously obtained from an animal host, said method comprising the steps of:
(a) lysing host cells present within the sample, wherein said lysing comprises adding a cytolysin to the sample;
(b) carrying-out a process to physically deplete at least genomic nucleic acid released from host cells within said sample or otherwise render such nucleic acid unidentifiable;
(c) depleting host mitochondria or host mitochondrial deoxyribonucleic acid (mtDNA) present in the treated sample, wherein said depleting host mitochondria or mtDNA comprises adding a detergent and a nuclease to the sample; and
(d) extracting and/or analysing remaining nucleic acid from the sample, wherein step (b) is performed before or after step (c).

9. The method according to claim 8, wherein step (a) comprises lysing at least 3% of the host cells in the sample.

10. The method according to claim 8, wherein the cytolysin comprises a phospholipase C.

11. The method according to claim 8, wherein the method results in at least a 5-fold depletion of host mitochondrial DNA originally contained within the sample.

12. The method according to claim 8, wherein the method further comprises amplifying and/or purifying the remaining nucleic acid.

13. The method according to claim 8, wherein the method further comprises sequencing the remaining nucleic acid or the amplified and/or extracted product thereof.

14. The method according to claim 13, wherein said sequencing identifies at least one drug resistance-conferring sequence in a pathogen present in the original sample.

15. The method according to claim 8, wherein the extracted remaining nucleic acid is bacterial, viral and/or fungal.

16. The method of claim 8, wherein the biological sample is blood.

17. The method of claim 8, wherein step (b) is performed before step (c), and the method further comprises performing a buffer exchange after the process to physically deplete genomic nucleic acid.

18. The method of claim 17, wherein the process to physically deplete genomic nucleic acid comprises adding a nuclease.

19. The method of claim 18, wherein the biological sample is blood.

* * * * *

SEQUENCE LISTING

```
<160> NUMBER OF SEQ ID NOS: 5

<210> SEQ ID NO 1
<211> LENGTH: 398
<212> TYPE: PRT
<213> ORGANISM: Clostridium perfringens

<400> SEQUENCE: 1

Met Lys Arg Lys Ile Cys Lys Ala Leu Ile Cys Ala Ala Leu Ala Thr
1               5                   10                  15

Ser Leu Trp Ala Gly Ala Ser Thr Lys Val Tyr Ala Trp Asp Gly Lys
            20                  25                  30

Ile Asp Gly Thr Gly Thr His Ala Met Ile Val Thr Gln Gly Val Ser
        35                  40                  45

Ile Leu Glu Asn Asp Met Ser Lys Asn Glu Pro Glu Ser Val Arg Lys
    50                  55                  60

Asn Leu Glu Ile Leu Lys Glu Asn Met His Glu Leu Gln Leu Gly Ser
65                  70                  75                  80

Thr Tyr Pro Asp Tyr Asp Lys Asn Ala Tyr Asp Leu Tyr Gln Asp His
                85                  90                  95

Phe Trp Asp Pro Asp Thr Asp Asn Asn Phe Ser Lys Asp Asn Ser Trp
            100                 105                 110

Tyr Leu Ala Tyr Ser Ile Pro Asp Thr Gly Glu Ser Gln Ile Arg Lys
        115                 120                 125

Phe Ser Ala Leu Ala Arg Tyr Glu Trp Gln Arg Gly Asn Tyr Lys Gln
```

```
                130                 135                 140
Ala Thr Phe Tyr Leu Gly Glu Ala Met His Tyr Phe Gly Asp Ile Asp
145                 150                 155                 160

Thr Pro Tyr His Pro Ala Asn Val Thr Ala Val Asp Ser Ala Gly His
                165                 170                 175

Val Lys Phe Glu Thr Phe Ala Glu Arg Lys Glu Gln Tyr Lys Ile
            180                 185                 190

Asn Thr Ala Gly Cys Lys Thr Asn Glu Asp Phe Tyr Ala Asp Ile Leu
                195                 200                 205

Lys Asn Lys Asp Phe Asn Ala Trp Ser Lys Glu Tyr Ala Arg Gly Phe
            210                 215                 220

Ala Lys Thr Gly Lys Ser Ile Tyr Tyr Ser His Ala Ser Met Ser His
225                 230                 235                 240

Ser Trp Asp Asp Trp Asp Tyr Ala Ala Lys Val Thr Leu Ala Asn Ser
                245                 250                 255

Gln Lys Gly Thr Ala Gly Tyr Ile Tyr Arg Phe Leu His Asp Val Ser
            260                 265                 270

Glu Gly Asn Asp Pro Ser Val Gly Lys Asn Val Lys Glu Leu Val Ala
            275                 280                 285

Tyr Ile Ser Thr Ser Gly Glu Lys Asp Ala Gly Thr Asp Asp Tyr Met
290                 295                 300

Tyr Phe Gly Ile Lys Thr Lys Asp Gly Lys Thr Gln Glu Trp Glu Met
305                 310                 315                 320

Asp Asn Pro Gly Asn Asp Phe Met Thr Gly Ser Lys Asp Thr Tyr Thr
                325                 330                 335

Phe Lys Leu Lys Asp Glu Asn Leu Lys Ile Asp Asp Ile Gln Asn Met
            340                 345                 350

Trp Ile Arg Lys Arg Lys Tyr Thr Ala Phe Pro Asp Ala Tyr Lys Pro
            355                 360                 365

Glu Asn Ile Lys Val Ile Ala Asn Gly Lys Val Val Val Asp Lys Asp
            370                 375                 380

Ile Asn Glu Trp Ile Ser Gly Asn Ser Thr Tyr Asn Ile Lys
385                 390                 395

<210> SEQ ID NO 2
<211> LENGTH: 319
<212> TYPE: PRT
<213> ORGANISM: Staphylococcus aureus

<400> SEQUENCE: 2

Met Lys Thr Arg Ile Val Ser Ser Val Thr Thr Leu Leu Leu Gly
1                   5                   10                  15

Cys Ile Leu Met Asn Pro Val Ala Asn Ala Ala Asp Ser Asp Ile Asn
                20                  25                  30

Ile Lys Thr Gly Thr Thr Asp Ile Gly Ser Asn Thr Thr Val Lys Thr
            35                  40                  45

Gly Asp Leu Val Thr Tyr Asp Lys Glu Asn Gly Met His Lys Lys Val
        50                  55                  60

Phe Tyr Ser Phe Ile Asp Asp Lys Asn His Asn Lys Lys Ile Leu Val
65                  70                  75                  80

Ile Arg Thr Lys Gly Thr Ile Ala Gly Gln Tyr Arg Val Tyr Ser Glu
                85                  90                  95

Glu Gly Ala Asn Lys Ser Gly Leu Ala Trp Pro Ser Ala Phe Lys Val
            100                 105                 110
```

```
Gln Leu Gln Leu Pro Asp Asn Glu Val Ala Gln Ile Ser Asp Tyr Tyr
            115                 120                 125

Pro Arg Asn Ser Ile Asp Thr Lys Glu Tyr Met Ser Thr Leu Thr Tyr
130                 135                 140

Gly Phe Asn Gly Asn Val Thr Gly Asp Asp Ser Gly Lys Ile Gly Gly
145                 150                 155                 160

Leu Ile Gly Ala Asn Val Ser Ile Gly His Thr Leu Lys Tyr Val Gln
                165                 170                 175

Pro Asp Phe Lys Thr Ile Leu Glu Ser Pro Thr Asp Lys Lys Val Gly
            180                 185                 190

Trp Lys Val Ile Phe Asn Asn Met Val Asn Gln Asn Trp Gly Pro Tyr
        195                 200                 205

Asp Arg Asp Ser Trp Asn Pro Val Tyr Gly Asn Gln Leu Phe Met Lys
210                 215                 220

Thr Arg Asn Gly Ser Met Lys Ala Ala Asp Asn Phe Leu Asp Pro Asn
225                 230                 235                 240

Lys Ala Ser Ser Leu Leu Ser Ser Gly Phe Ser Pro Asp Phe Ala Thr
                245                 250                 255

Val Ile Thr Met Asp Arg Lys Ala Ser Lys Gln Gln Thr Asn Ile Asp
            260                 265                 270

Val Ile Tyr Glu Arg Val Arg Asp Asp Tyr Gln Leu Tyr Trp Thr Ser
        275                 280                 285

Thr Asn Trp Lys Gly Thr Asn Thr Lys Asp Lys Trp Thr Asp Arg Ser
290                 295                 300

Ser Glu Arg Tyr Lys Ile Asp Trp Glu Lys Glu Glu Met Thr Asn
305                 310                 315

<210> SEQ ID NO 3
<211> LENGTH: 571
<212> TYPE: PRT
<213> ORGANISM: Streptococcus pyogenes

<400> SEQUENCE: 3

Met Ser Asn Lys Lys Thr Phe Lys Lys Tyr Ser Arg Val Ala Gly Leu
1               5                   10                  15

Leu Thr Ala Ala Leu Ile Ile Gly Asn Leu Val Thr Ala Asn Ala Glu
            20                  25                  30

Ser Asn Lys Gln Asn Thr Ala Ser Thr Glu Thr Thr Thr Thr Ser Glu
        35                  40                  45

Gln Pro Lys Pro Glu Ser Ser Glu Leu Thr Ile Glu Lys Ala Gly Gln
    50                  55                  60

Lys Met Asp Asp Met Leu Asn Ser Asn Asp Met Ile Lys Leu Ala Pro
65                  70                  75                  80

Lys Glu Met Pro Leu Glu Ser Ala Glu Lys Glu Lys Lys Ser Glu
                85                  90                  95

Asp Lys Lys Lys Ser Glu Glu Asp His Thr Glu Glu Ile Asn Asp Lys
            100                 105                 110

Ile Tyr Ser Leu Asn Tyr Asn Glu Leu Glu Val Leu Ala Lys Asn Gly
        115                 120                 125

Glu Thr Ile Glu Asn Phe Val Pro Lys Glu Gly Val Lys Lys Ala Asp
    130                 135                 140

Lys Phe Ile Val Ile Glu Arg Lys Lys Asn Ile Asn Thr Thr Pro
145                 150                 155                 160

Val Asp Ile Ser Ile Ile Asp Ser Val Thr Asp Arg Thr Tyr Pro Ala
                165                 170                 175
```

Ala Leu Gln Leu Ala Asn Lys Gly Phe Thr Glu Asn Lys Pro Asp Ala
            180                 185                 190

Val Val Thr Lys Arg Asn Pro Gln Lys Ile His Ile Asp Leu Pro Gly
            195                 200                 205

Met Gly Asp Lys Ala Thr Val Glu Val Asn Asp Pro Thr Tyr Ala Asn
210                 215                 220

Val Ser Thr Ala Ile Asp Asn Leu Val Asn Gln Trp His Asp Asn Tyr
225                 230                 235                 240

Ser Gly Gly Asn Thr Leu Pro Ala Arg Thr Gln Tyr Thr Glu Ser Met
                245                 250                 255

Val Tyr Ser Lys Ser Gln Ile Glu Ala Ala Leu Asn Val Asn Ser Lys
            260                 265                 270

Ile Leu Asp Gly Thr Leu Gly Ile Asp Phe Lys Ser Ile Ser Lys Gly
            275                 280                 285

Glu Lys Lys Val Met Ile Ala Ala Tyr Lys Gln Ile Phe Tyr Thr Val
    290                 295                 300

Ser Ala Asn Leu Pro Asn Asn Pro Ala Asp Val Phe Asp Lys Ser Val
305                 310                 315                 320

Thr Phe Lys Asp Leu Gln Arg Lys Gly Val Ser Asn Glu Ala Pro Pro
                325                 330                 335

Leu Phe Val Ser Asn Val Ala Tyr Gly Arg Thr Val Phe Val Lys Leu
            340                 345                 350

Glu Thr Ser Ser Lys Ser Asn Asp Val Glu Ala Ala Phe Ser Ala Ala
            355                 360                 365

Leu Lys Gly Thr Asp Val Lys Thr Asn Gly Lys Tyr Ser Asp Ile Leu
    370                 375                 380

Glu Asn Ser Ser Phe Thr Ala Val Val Leu Gly Gly Asp Ala Ala Glu
385                 390                 395                 400

His Asn Lys Val Val Thr Lys Asp Phe Asp Val Ile Arg Asn Val Ile
                405                 410                 415

Lys Asp Asn Ala Thr Phe Ser Arg Lys Asn Pro Ala Tyr Pro Ile Ser
            420                 425                 430

Tyr Thr Ser Val Phe Leu Lys Asn Asn Lys Ile Ala Gly Val Asn Asn
            435                 440                 445

Arg Thr Glu Tyr Val Glu Thr Thr Ser Thr Glu Tyr Thr Ser Gly Lys
    450                 455                 460

Ile Asn Leu Ser His Gln Gly Ala Tyr Val Ala Gln Tyr Glu Ile Leu
465                 470                 475                 480

Trp Asp Glu Ile Asn Tyr Asp Asp Lys Gly Lys Glu Val Ile Thr Lys
                485                 490                 495

Arg Arg Trp Asp Asn Asn Trp Tyr Ser Lys Thr Ser Pro Phe Ser Thr
            500                 505                 510

Val Ile Pro Leu Gly Ala Asn Ser Arg Asn Ile Arg Ile Met Ala Arg
            515                 520                 525

Glu Cys Thr Gly Leu Ala Trp Glu Trp Trp Arg Lys Val Ile Asp Glu
    530                 535                 540

Arg Asp Val Lys Leu Ser Lys Glu Ile Asn Val Asn Ile Ser Gly Ser
545                 550                 555                 560

Thr Leu Ser Pro Tyr Gly Ser Ile Thr Tyr Lys
                565                 570

<210> SEQ ID NO 4
<211> LENGTH: 331

```
<212> TYPE: PRT
<213> ORGANISM: Staphylococcus aureus

<400> SEQUENCE: 4

Met Met Val Lys Lys Thr Lys Ser Asn Ser Leu Lys Lys Val Ala Thr
1               5                   10                  15

Leu Ala Leu Ala Asn Leu Leu Val Gly Ala Leu Thr Asp Asn Ser
            20                  25                  30

Ala Lys Ala Glu Ser Lys Lys Asp Asp Thr Asp Leu Lys Leu Val Ser
            35                  40                  45

His Asn Val Tyr Met Leu Ser Thr Val Leu Tyr Pro Asn Trp Gly Gln
        50                  55                  60

Tyr Lys Arg Ala Asp Leu Ile Gly Gln Ser Ser Tyr Ile Lys Asn Asn
65                  70                  75                  80

Asp Val Val Ile Phe Asn Glu Ala Phe Asp Asn Gly Ala Ser Asp Lys
                85                  90                  95

Leu Leu Ser Asn Val Lys Lys Glu Tyr Pro Tyr Gln Thr Pro Val Leu
            100                 105                 110

Gly Arg Ser Gln Ser Gly Trp Asp Lys Thr Glu Gly Ser Tyr Ser Ser
        115                 120                 125

Thr Val Ala Glu Asp Gly Gly Val Ala Ile Val Ser Lys Tyr Pro Ile
130                 135                 140

Lys Glu Lys Ile Gln His Val Phe Lys Ser Gly Cys Gly Phe Asp Asn
145                 150                 155                 160

Asp Ser Asn Lys Gly Phe Val Tyr Thr Lys Ile Glu Lys Asn Gly Lys
                165                 170                 175

Asn Val His Val Ile Gly Thr His Thr Gln Ser Glu Asp Ser Arg Cys
            180                 185                 190

Gly Ala Gly His Asp Arg Lys Ile Arg Ala Glu Gln Met Lys Glu Ile
        195                 200                 205

Ser Asp Phe Val Lys Lys Asn Ile Pro Lys Asp Glu Thr Val Tyr
210                 215                 220

Ile Gly Gly Asp Leu Asn Val Asn Lys Gly Thr Pro Glu Phe Lys Asp
225                 230                 235                 240

Met Leu Lys Asn Leu Asn Val Asn Asp Val Leu Tyr Ala Gly His Asn
                245                 250                 255

Ser Thr Trp Asp Pro Gln Ser Asn Ser Ile Ala Lys Tyr Asn Tyr Pro
            260                 265                 270

Asn Gly Lys Pro Glu His Leu Asp Tyr Ile Phe Thr Asp Lys Asp His
        275                 280                 285

Lys Gln Pro Lys Gln Leu Val Asn Glu Val Thr Glu Lys Pro Lys
290                 295                 300

Pro Trp Asp Val Tyr Ala Phe Pro Tyr Tyr Val Tyr Asn Asp Phe
305                 310                 315                 320

Ser Asp His Tyr Pro Ile Lys Ala Tyr Ser Lys
                325                 330

<210> SEQ ID NO 5
<211> LENGTH: 553
<212> TYPE: PRT
<213> ORGANISM: Streptomyces vinaceus

<400> SEQUENCE: 5

Met His Arg His Thr Pro Ser Leu Arg Arg Pro Ser Ala His Leu Pro
1               5                   10                  15
```

-continued

```
Ser Ala Leu Ala Val Arg Ala Ala Val Pro Ala Ala Leu Leu Ala Leu
         20                  25                  30
Phe Ala Ala Val Pro Ala Ser Ala Pro Ala Ala Gly Ser Gly Ala
         35                  40                  45
Asp Pro Ala Pro His Leu Asp Ala Val Glu Gln Thr Leu Arg Gln Val
 50                  55                  60
Ser Pro Gly Leu Glu Gly Gln Val Trp Glu Arg Thr Ala Gly Asn Val
 65                  70                  75                  80
Leu Asp Ala Ser Thr Pro Gly Gly Ala Asp Trp Leu Leu Gln Thr Pro
                 85                  90                  95
Gly Cys Trp Gly Asp Asp Lys Cys Thr Ala Arg Pro Gly Thr Glu Gln
                100                 105                 110
Leu Leu Ser Lys Met Thr Gln Asn Ile Ser Gln Ala Thr Arg Thr Val
            115                 120                 125
Asp Ile Ser Thr Leu Ala Pro Phe Pro Asn Gly Ala Phe Gln Asp Ala
            130                 135                 140
Ile Val Ser Gly Leu Lys Thr Ser Ala Ala Arg Gly Asn Lys Leu Lys
145                 150                 155                 160
Val Arg Val Leu Val Gly Ala Ala Pro Val Tyr His Leu Asn Val Leu
                165                 170                 175
Pro Ser Lys Tyr Arg Asp Glu Leu Val Ala Lys Leu Gly Ala Asp Ala
                180                 185                 190
Arg Asn Val Asp Leu Asn Val Ala Ser Met Thr Thr Ser Lys Thr Ala
            195                 200                 205
Phe Ser Trp Asn His Ser Lys Leu Leu Val Val Asp Gly Gln Ser Val
            210                 215                 220
Ile Thr Gly Gly Ile Asn Asp Trp Lys Asp Asp Tyr Leu Glu Thr Ala
225                 230                 235                 240
His Pro Val Ala Asp Val Asp Leu Ala Leu Arg Gly Pro Ala Ala Ala
                245                 250                 255
Ser Ala Gly Arg Tyr Leu Asp Glu Leu Trp Ser Trp Thr Cys Gln Asn
                260                 265                 270
Lys Ser Asn Ile Ala Ser Val Trp Phe Ala Ser Ser Asn Gly Ala Ala
            275                 280                 285
Cys Met Pro Ala Met Ala Lys Asp Thr Ala Pro Ala Ala Pro Ala Pro
            290                 295                 300
Ala Pro Gly Asp Val Pro Val Ala Val Gly Gly Leu Gly Val Gly Val
305                 310                 315                 320
Ile Lys Arg Asn Asp Pro Ser Ser Ser Phe Arg Pro Ala Leu Pro Ser
                325                 330                 335
Ala Pro Asp Thr Lys Cys Val Val Gly Leu His Asp Asn Thr Asn Ala
            340                 345                 350
Asp Arg Asp Tyr Asp Thr Val Asn Pro Glu Glu Ser Ala Leu Arg Thr
        355                 360                 365
Leu Ile Ser Ser Ala Asn Arg His Ile Glu Ile Ser Gln Gln Asp Val
        370                 375                 380
Asn Ala Thr Cys Pro Pro Leu Pro Arg Tyr Asp Ile Arg Val Tyr Asp
385                 390                 395                 400
Ala Leu Ala Ala Arg Met Ala Ala Gly Val Lys Val Arg Ile Val Val
                405                 410                 415
Ser Asp Pro Ala Asn Arg Gly Ala Val Gly Ser Gly Gly Tyr Ser Gln
                420                 425                 430
Ile Lys Ser Leu Ser Glu Ile Ser Asp Thr Leu Arg Asp Arg Leu Ala
```

-continued

```
                 435                 440                 445
Leu Val Thr Gly Asp Gln Gly Ala Ala Lys Ala Thr Met Cys Ser Asn
    450                 455                 460

Leu Gln Leu Ala Thr Phe Arg Ser Ser Gln Ser Pro Thr Trp Ala Asp
465                 470                 475                 480

Gly His Pro Tyr Ala Gln His His Lys Val Val Ser Val Asp Asp Ser
                485                 490                 495

Ala Phe Tyr Ile Gly Ser Lys Asn Leu Tyr Pro Ala Trp Leu Gln Asp
                500                 505                 510

Phe Gly Tyr Val Val Glu Ser Pro Ala Ala Ala Gln Leu Asn Ala
                515                 520                 525

Arg Leu Leu Ala Pro Gln Trp Gln Tyr Ser Arg Ala Thr Ala Thr Ile
    530                 535                 540

Asp His Glu Arg Ala Leu Cys Gln Ser
545                 550
```